US008394815B2

(12) United States Patent
Al-Qawasmeh et al.

(10) Patent No.: US 8,394,815 B2
(45) Date of Patent: *Mar. 12, 2013

(54) 2,4,5-TRISUBSTITUTED IMIDAZOLES AND THEIR USE AS ANTI-MICROBIAL AGENTS

(75) Inventors: Raed H. Al-Qawasmeh, North York (CA); Aiping H. Young, Toronto (CA); Mario Huesca, Toronto (CA); Yoon S. Lee, Mississauga (CA)

(73) Assignee: Lorus Therapeutics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/976,122

(22) Filed: Dec. 22, 2010

(65) Prior Publication Data

US 2011/0152337 A1 Jun. 23, 2011

Related U.S. Application Data

(62) Division of application No. 10/525,690, filed as application No. PCT/CA03/01229 on Aug. 19, 2003, now Pat. No. 7,884,120.

(30) Foreign Application Priority Data

Aug. 19, 2002 (CA) ..................................... 2398765

(51) Int. Cl.
C07D 471/12 (2006.01)
A61K 31/435 (2006.01)
A61P 31/04 (2006.01)
(52) U.S. Cl. .......................... 514/287; 546/64
(58) Field of Classification Search .................. None
See application file for complete search history.

(56) References Cited

U.S. PATENT DOCUMENTS

| 3,279,918 | A | 10/1966 | Cassiers et al. |
| 3,297,710 | A | 1/1967 | Silversmith |
| 3,714,181 | A | 1/1973 | Lantos |
| 4,089,747 | A | 5/1978 | Bruschi |
| 4,423,046 | A | 12/1983 | Carlson |
| 4,466,976 | A | 8/1984 | Klose et al. |
| 4,585,771 | A | 4/1986 | Klose et al. |
| 4,705,855 | A | 11/1987 | Desideri et al. |
| 4,721,670 | A | 1/1988 | Osada et al. |
| 4,902,705 | A | 2/1990 | Hirota et al. |
| 4,970,226 | A | 11/1990 | Sun |
| 5,011,472 | A | 4/1991 | Aeblscher |
| 5,023,252 | A | 6/1991 | Hsieh |
| 5,024,935 | A | 6/1991 | McClune |
| 5,047,318 | A | 9/1991 | Snyder |
| 5,496,702 | A | 3/1996 | Bishop |
| 5,514,550 | A | 5/1996 | Findlay |
| 5,656,644 | A | 8/1997 | Adams |
| 5,686,455 | A | 11/1997 | Adams |
| 5,693,589 | A | 12/1997 | Goswaml |
| 5,700,826 | A | 12/1997 | Mjalli et al. |
| 5,753,687 | A | 5/1998 | Mjalli |
| 5,916,891 | A | 6/1999 | Adams |
| 5,945,418 | A | 8/1999 | Bemis |
| 6,060,216 | A | 5/2000 | Ichikawa |
| 6,117,609 | A | 9/2000 | Maeda |
| 6,194,441 | B1 | 2/2001 | Roberts |
| 6,268,370 | B1 | 7/2001 | Adams |
| 6,288,212 | B1 | 9/2001 | Hancock |
| 6,521,655 | B1 | 2/2003 | Beers |
| 7,115,645 | B2 | 10/2006 | Halfbrodt et al. |
| 7,291,404 | B2 | 11/2007 | Aziz et al. |
| 7,718,685 | B2 * | 5/2010 | Shin et al. ..................... 514/396 |
| 7,884,120 | B2 * | 2/2011 | Al-Qawasmeh et al. ..... 514/393 |
| 7,888,118 | B2 * | 2/2011 | Shin et al. ..................... 435/377 |
| 7,989,089 | B2 * | 8/2011 | Wang et al. .................... 428/690 |
| 8,148,392 | B2 * | 4/2012 | Huesca et al. ................. 514/287 |
| 2004/0176601 | A1 | 9/2004 | Goulet |
| 2004/0265628 | A1 | 12/2004 | Wang et al. |

FOREIGN PATENT DOCUMENTS

| CA | 1195325 B1 | 10/1985 |
| CA | 2351694 A1 | 7/1993 |
| CN | 1289774 | 9/1999 |
| CN | 1289775 | 9/1999 |
| DE | 3141063 A1 | 10/1985 |
| EP | 0077024 | 4/1983 |
| EP | 165588 A2 | 12/1985 |
| EP | 0812829 A1 | 12/1997 |
| EP | 1428831 | 6/2004 |
| JP | 11199582 | 7/1999 |
| JP | 2000273088 | 10/2000 |
| JP | 2002275458 A1 | 9/2002 |
| WO | WO 9314081 A1 | 7/1993 |
| WO | WO 9503297 A1 | 2/1995 |
| WO | WO 9618626 A1 | 6/1996 |
| WO | WO 9736587 A1 | 10/1997 |
| WO | WO 9827065 A1 | 6/1998 |
| WO | WO 9827108 A2 | 6/1998 |
| WO | WO 9901128 A1 | 1/1999 |
| WO | WO 9902155 A1 | 1/1999 |
| WO | WO 9907701 A1 | 2/1999 |
| WO | WO 0059541 A1 | 3/2000 |
| WO | WO 0033836 A1 | 6/2000 |

(Continued)

OTHER PUBLICATIONS

Kimura et al., New Technologies & Medicine, 2002, 3(1):30-34.
Moylan et al., Chemistry of Materials, 1993, 5(10):1499-1508.
Pechkin, A.A. et. al., Synthesis and Properties of 2-(2-Furyl)-and 2-(2-Thienyl)-1-methylphenanthro[9,10-d]imidazoles, Russian Journal of Organic Chemistry (Translation of Zhurnal Organicheskoi Khimii), 2002, 38(5):726-730.
Xu et al., New J. Chem., 2003, 27:1255-1263.

(Continued)

*Primary Examiner* — Fiona T Powers
(74) *Attorney, Agent, or Firm* — McAndrews, Held & Malloy Ltd.

(57) ABSTRACT

The present invention provides therapeutically effective 2,4,5-trisubstituted imidazole compounds, methods of preparing the same, and compositions comprising the compounds alone or in combination with other agents. The present invention further provides for the use of the compounds as anti-microbial agents. The anti-microbial properties of the compounds include anti-bacterial and/or anti-fungal activity.

15 Claims, 1 Drawing Sheet

FOREIGN PATENT DOCUMENTS

| | | |
|---|---|---|
| WO | WO 0068206 | 11/2000 |
| WO | WO 0068266 | 11/2000 |
| WO | WO 0078761 | 12/2000 |
| WO | WO 0126467 A1 | 4/2001 |
| WO | WO 0224680 A1 | 3/2002 |
| WO | WO 0246168 A1 | 6/2002 |
| WO | 02072576 | 9/2002 |
| WO | WO 02083111 A2 | 10/2002 |
| WO | WO 03004023 A1 | 1/2003 |
| WO | 03032984 | 4/2003 |
| WO | 03066579 | 8/2003 |
| WO | WO 03087026 A1 | 10/2003 |
| WO | 2004005264 | 1/2004 |
| WO | WO 2004005264 A2 | 1/2004 |
| WO | 2004016086 | 2/2004 |
| WO | WO 2004016086 A2 | 2/2004 |
| WO | WO 2005047266 A1 | 5/2005 |

OTHER PUBLICATIONS

Zeytinogiu et al., Drug and Chemical Toxicology, 2003, 26(4):245-257.
Office Action dated Dec. 31, 2007, for U.S. Appl. No. 10/579,149.
Office Action dated Dec. 8, 2008, for U.S. Appl. No. 10/579,149.
Office Action dated Jun. 8, 2009, for U.S. Appl. No. 10/579,149.
Office Action dated Jan. 8, 2010, for U.S. Appl. No. 10/579,149.
Office Action dated Jul. 20, 2009 for U.S. Appl. No. 10/525,590.
Office Action dated Nov. 18, 2009 for U.S. Appl. No. 10/525,590.
Registry No. 330449-64-4 entered into Registry File in STN on Apr. 6, 2001.
Registry No. 416872-13-4 entered into Registry File in STN on May 16, 2002.
Office Action dated Dec. 14, 2009 for U.S. Appl. No. 10/525,690.
Office Action dated Jun. 4, 2010 for U.S. Appl. No. 10/525,690.
Written Opinion mailed on May 24, 2004 for International Application No. PCT/CA03/01229.
Office Action dated Dec. 31, 2007 for U.S. Appl. No. 10/579,149.
Tanaseichuk et al.; Uch. Zap., Mord. Univ. (1971), No. 81,95-7 (From: Ref. Zh., Khim. 1972, Abstr. No. 12zh318 (English abstract).
Registry No. 330449-52-0 entered into Registry File in STN on Apr. 6, 2001.
Registry No. 332148-67-1 entered into Registry File in STN on Apr. 24, 2001.
Registry No. 404904-57-0 entered into Registry File in STN on Apr. 10, 2002.
Registry No. 309285-51-6 entered into Registry File in STN on Dec. 18, 2000.
John Lewis; Muscarine, imidazole, oxazole, thiazole and peptide alkaloids, and other miscellaneous alkaloids; Natural Product Reports; 1998; 15: 417-437; Royal Society of Chemistry; London, UK.
John Lewis; Muscarine, imidazole, oxazole, thiazole and peptide alkaloids, and other miscellaneous alkaloids; Natural Product Reports; 1998; 15: 371-395; Royal Society of Chemistry; London, UK.
John Lewis; Miscellaneous alkaloids: Amaryllidaceae, Sceletium, muscarine, imidazole, oxazole, peptide and other miscellaneous alkaloids; Natural Product Reports; 1999; 16: 389-416; Royal Society of Chemistry; London, UK.
LoGrasso et al; Kinetic Mechanism for p38 MAP Kinase; Biochemistry; 1997; 36: 10422-10427; American Chemical Society; Rahway, New Jersey, USA.
Low et al; Clinical Prevalence, Antimicrobial Susceptibility, and Geographic Resistance Patterns of Enterococci: Results from the SENTRY Antimicrobial Surveillance Program, 1997-1999; Clinical Infectious Diseases; 2001; 32: S133-145; University of Chicago Press; Chicago, IL, USA.
McLay et al; The Discovery of RPR 200765A, a p38 MAP Kinase Inhibitor Displaying a Good Oral Anti-Arthritic Efficacy; Bioorganic & Medicinal Chemistry; 2001; 9: 537-554; Elsevier Science Ltd; Amsterdam, The Netherlands.
Hamish R. Michie; The value of animal models in the development of new drugs for the treatment of the sepsis syndrome; Journal for Antimicrobial Chemotherapy; 1998; 41: 47-49; British Society for Antimicrobial Chemotherapy; Birmingham, UK.
Michael A. Pfaller, MD and Wen Liang Yu, MD; Antifungal Susceptibility Testing; Infectious Disease Clinics of North America; 2001; 15: 1227-145; Elsevier; Philadelphia, PA, USA.
Pfaller et al; Antifungal Susceptibility Testing: Technical Advances and Potential Clinical Applications; Clinical Infectious Diseases; 1997; 24: 776-84; University of Chicago Press; Chicago, IL, USA.
Sarshar et al.; Imidazole Libraries on Solid Support; Tetrahedron Letters; 1996; 37: 835-838; Elsevier Science Ltd.; London, UK.
Shibata et al.; Therapeutic efficacy of J-111, 225, a novel trans-3, 5-disubstituted pyrrolidinylthio-1 methylcarbapenem, against experimental murine systemic Infections; Journal of Antimicrobial Chemotherapy; 2000; 45: 379-82; British Society for Antimicrobial Chemotherapy; Birmingham, UK.
Simor et al.; 1999 Canada Communicable Disease Report; 25: 105-108.
Steve Sternberg; The Emerging Fungal Threat Science; 1994; 266:1632-1634; American Association for the Advancement of Science; Washington, DC, USA.
Thaler et al.; Evaluation of Single-Drug and Combination Antifungal Therapy in an Experimental Model of Candidiasis in Rabbits with Prolonged Neutropenia; The Journal of Infectious Diseases; 1988; 158: 80-88; University of Chicago Press; Chicago, IL, USA.
Dora, E.K. et al., Synthesis of Some Fused 2-arylimidazoles and their Derivatives, Journal of Indian Chemical Society, 1979, 56(6):620-624.
Walsh et al.; Effects of Preventive, Early, and Late Antifungal Chemotherapy with Fluconazole in Different Granulocytopenic Models of Experimental Disseminated Candidiasis; The Journal of Infectious Diseases; 1990; 161: 755-760; University of Chicago Press; Chicago, IL, USA.
Yanke et al.; A CD-1 mouse model of infection with *Staphylococcus aureus*: Influence of gender on Infection with MRSA and MSSA isolates; Canada Journal of Microbiology; 2000; 46:920-926; NRC Research Press website.
Zhang et al; 2,4,5-Trisubstituted Imidazoles: Novel Nontoxic Modulators of P-glycoprotein Mediated Multidrug Resistance. Part 2; Bioorganic & Medicinal Chemistry Letters; 2000; 10: 2603-2605; Elsevier Science Ltd; Philadelphia, PA, USA.
Ghannoum et al; Susceptibility Testing of Fungi: Current Status of Correlation of In Vitro Data with Clinical Outcome; Journal of Clinical Microbiology; 1996; 34: 489-495; American Society for Microbiology; Washington, DC, USA.
Antolini et al; Analogues of 4,5-bis(3,5-Dichlorophenyl)-2-Trifluoromethyl-1 H-Imidazole as Potential Antibacterial Agents; Bioorganic and Medicinal Chemistry Letters; Apr. 1999; 9(7):1023-1028; Elsevier Science Ltd; Philadelphia, PA, USA.
Isikdag et al; QSAR of Inhibitory Activities by 2,4,5-Trisubstituted Imidazole Derivatives on Tubifex Worms; Acta Pharmaceutica Turcica; 1995; 37(1):19-24.
B. Krieg and G. Manecke; Synthese and Halbleitereigenschaften arylsubstitulerter Imidazole; Naturforsch; 1967; 22b: 132-141.
Abel-Meguid et al.; An Orally Bioavailable HIV-1 Protease Inhibitor Containing an Imidazole-Derived Peptide Bond Replacement: Crystallographic and Pharmacokinetic Analysis; Biochemistry; 1994: 33; 11671-11677; American Chemical Society.
Adams et al; Pyrimidinylimidazole Inhibitors of p38: Cyclic N-1 Imidazole Substituents Enhance p38 Kinase Inhibition and Oral Activity; Bioorganic and Medicinal Chemistry Letters; 2001; 11:2667-2870; Elsevier Science Ltd: Philadelphia, PA,USA.
Arroyo et al.; Therapy of Murine Aspergillosis with Amphotericin B in Combination with Rifampin or 5-25 Fluorocytosine; Antimicrobiai Agents and Chemotheraphy; 1977; pp. 21-25; American Society for Microbiology; Washington, DC, USA.
Xiu R. Bu et al; A Novel Approach to Synthesis of Tricyanovinylthiophene for heterocyclic Imidazole Nonlinear Optical Chromophores; Tetrahedron Letters; 1996; 37: 7331-7334; Elsevier Science Ltd; London, UK.
Chi, K.; Palladium Catalyst in DMSO for the Oxidation of Tolans to Benzils; Synthetic Communications; 1994; 24(15): 2119-2122; Marcel Dekker, Inc., now Taylor and Francis.

Cuenda et al; Activation of stress-activated protein kinase-3 (SAPK3) by cytokines and cellular stresses is mediated via SAPKK3 (MKK6); comparison of the specificities of SAPK3 and SAPK2 (RKIp38); The EMBO Journal; 1997; 16: 295-305; Oxford University Press; Oxford, UK.

Cuenda et al; SB 203580 is a specific inhibitor of a MAP kinase homologue which is stimulated by cellular stresses and interleukin-1; Federation of European Biochemical Societies Letters; 1995; 364: 229-33; Elsevier BV on behalf of Federation of European Biochemical Societies.

Diekema et al; Survey of Infections due to *Staphylococcus* Species: Frequency of Occurence and Antimicrobial Susceptibility of Isolates Collected in the United States, Canada, Latin America, Europe, and the Western Pacific Region for the SENTRY Antimicrobial Surveillance Program, 1997-1999; Clinical Infectious Diseases; 2001; 32: S114-132; University of Chicago Press; Chicago, IL, USA.

Ekwall, Bjorn; Screening of Toxic Compounds in Mammalian Cell Cultures; Annals New York Academy of Sciences; 1983; 407: 64-77; Blackwell Publishing.

Fishcer et al; Dissociation Constants of the Conjugate Acids of Substituted Benzyl Phenyl Ketones and of Alkyl-substituted Benzophenones; Journal of American Chemical Society; 1961; 83: 4208-4210; American Chemical Society; Washington, DC, USA.

Gales et al; Characterization of *Pseudomonas aeruginosa* Isolates: Occurence Rates, Antimicrobial Susceptibility Patterns, and Molecular Typing in the Global SENTRY Antimicrobial Survelliance Program, 1997-1999; Clinical Infectious Diseases; 2001; 32:S146-155; Infectious Disease Society of America; The University of Chicago Press; Chicago, IL, USA.

Goto et al; Improved efficacy with nonsimultaneous administration of netilmicin and minocycline against methicillin-resistant *Staphylococcus aureus* in in vitro and in vivo modeis; International Journal of Antimicrobial Agents; 1999; 11:39-46; International Society of Chemotherapy; Elsevier Science B.V.; United Kingdom.

Guijarro et al; The Reaction of Active Zinc with Organic Bromides; Journal of American Chemical Society; 1999; 121,4155-4157; American Chemical Society; Washington, DC, USA.

Heerding et al; 1,4 Disubstituted Imidazoles are Potential Antibacterial Agents Functioning as Inhibitors of Enoyl Acyl Carrier Protein Reductase (Fabl); Biorganic and Medicinal Chemistry Letters; 2001, 11:2061-2065; Elsevier Science Ltd; Philadelphia, PA, USA.

Hoban et al; Worldwide Prevalence of Antimicrobial Resistance in *Streptococcus pneumoniae, Haemophilus influenzae,* and *Moraxella catarrhalis* in the SENTRY Antimicrobial Surveillance Program, 1997-1999; Clinical Infectious Diseases; 2001: 32:S81-93; Infectious Disease Society of America; The University of Chicago Press; Chicago, IL, USA.

Huesca et al; Adhesion and Virulence Properties of Epidemic Canadian Methicillin-Resistant *Staphylococcus aureus* Strain 1: Identification of Novel Adhesion Functions Associated with Plasmin-Sensitive Surface Protein; The Journal of Infectious Disease; 2002; Infectious Diseases Society of America; The University of Chicago Press; Chicago, IL, USA.

Iwahi et ai; Virulence of *Escherichia coil* in Ascending Urinary-Tract Infection in Mice; Journal of Medical Microbiology; 1982; 15;303-316; The Society for General Microbiology; HIghWire Press.

Sarshar et al; 2,4,5-Trisubstituted Imidazoles; Novel Nontoxic Modulators of P-glycoprotein Mediated Multidrug Resistance. Part 1; Biorganic and Medicinal Chemistry Letters; 2000; 10;2599-2601; Elsevier Science Ltd; Philadeiphia, PA, USA.

Armesto et al; A New Site Selective Synthesis of Benzoin Esters, Synthesis of Symmetrically and Unsymmetrically Substituted Benzils; Synthesis; 1988; 799-801.

Totsuka et al., Combined effects of vancomycin and imipenem against methicillin-resistant *Staphylococcus aureus* (MRSA) in vitro and in vivo; Journal of Antimicrobial Chemotherapy; 1999; 44; 455-460; The British Society for Antimicrobial Chemotherapy; Birmingham, UK.

Bhaduri et al.; Potential Antifertility Agents; Syntheses of 2,4,5-substituted Imidazoles; Indian Journal of Chemistry; 1966; 4(9); 419-20; NISCAIR; New Delhi, India.

Database WPI; Section Ch. Week 199940, Derwent Publications Ltd., London, GB, AN 1999-474062 (XP002268773) & JP 11199582 (english abstract) (Sagami Chem Res Cent), Jul. 27, 1999.

Lechner et al.; Differential Production of TNK by Kupffer cells after phagocytosis of *E. coli* and *C. albicans*; American Journal of Physiology; 1994; 10;1-8; American Physiological Society.

Klose et al; The Suckling Mouse Model of Cholera; Trends in Microbiology; 2000; 8: 189-91; Elsevier Science Ltd.

Lee et al; A Protein Kinase Involved in the Regulation of Inflammatory Cytokine Biosynthesis; Nature; 1994; 327: 739-745 I&I.

C.G. Wermuth, Hiroshi Nagase (translation supervisor), Saishin Spyaku Kagaku, Jo kan, Tecnomics Corporation, 1998, p. 243-248 (Japanese version)—Corresponding to C.G. Wermuth, The Practice of Medicinal Chemistry, Molecular Variations Based on Isosteric Replacements, 1996, 203-247, Academic Press (English Version).

Chao et al., Polyhedron, 2000, 19:1975-1983.

Office Action dated Jun. 17, 2008, for U.S. Appl. No. 10/579,149.

Isikag et al., "Synthesis and analgesic activities of 2-substituted-1H-phenantro [9,10-d] imidazoles," Boll. Chim. Farmaceutico, 138:453-456 (1999).

Uchenye Zapiski 1971, 81 95-97.

Pozharskii et al., "Synthesis and Transformations fo 2-(2-Furyl)- and 2-[β-2-Furyl)Vinyl] Phenanthr [9,10] Imidazoles," Chern. Het. Comp., 7:950-952 (1971).

Sircar et al., "Dyes Derived from Phenanthraquinone. Part III. Phenanthriminazoles," J. Chern. Soc., 123:1559-1565 (1923).

Steck et al., "Reactions of Phenanthraquinone and Retenequinone with Aldehydes and Ammonium Acetate in Acetic Acid Solution," J. Am. Chem. Soc., 65:452-456 (1943).

Ito et al., "Photochemical Reaction of Imidazoles with Unsaturated Nitriles. Chemistry of Encounter Complex and Ion Pair," J. Org. Chern. 44:41-49 (1979).

Nippon Kagaku Zasshi 1971, 92, 365-370.

* cited by examiner

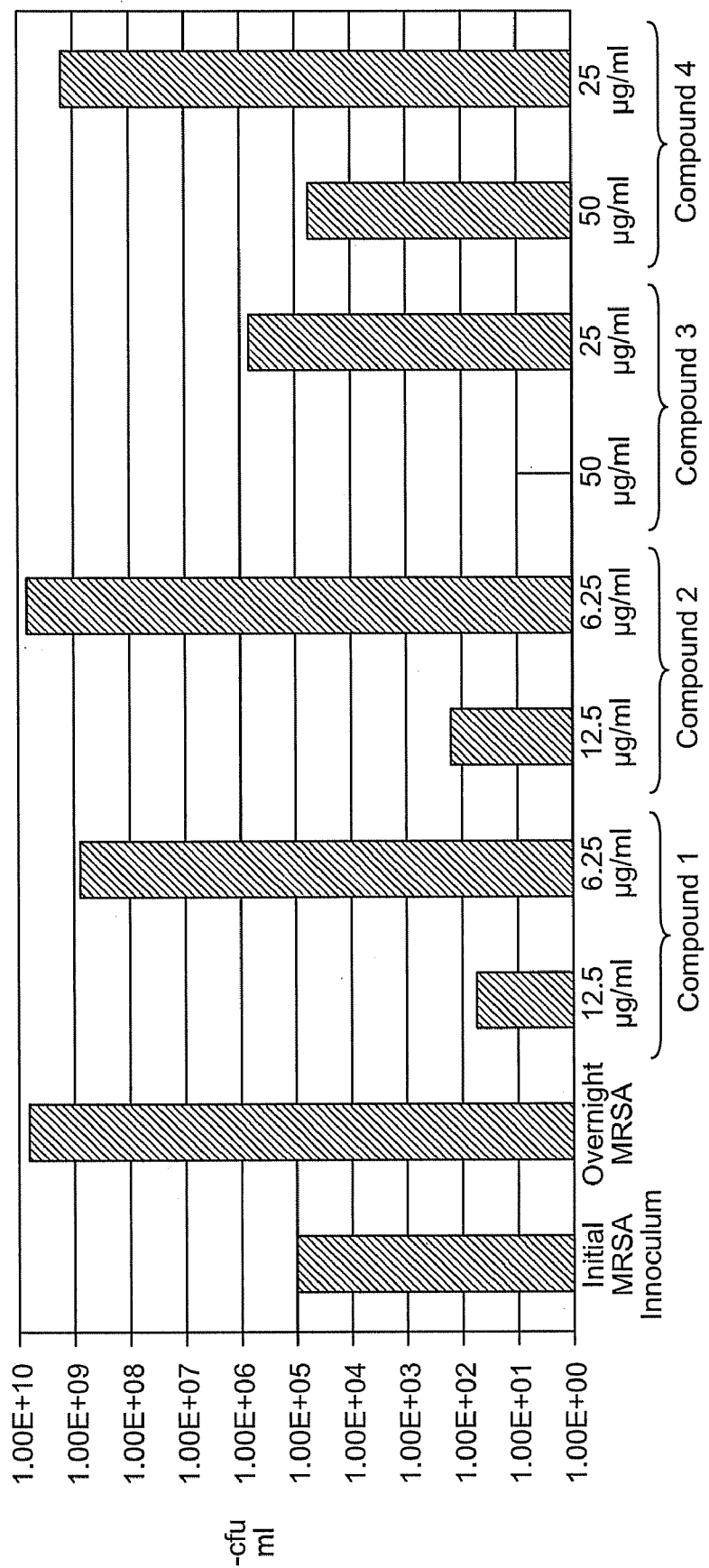

2,4,5-TRISUBSTITUTED IMIDAZOLES AND THEIR USE AS ANTI-MICROBIAL AGENTS

CROSS-REFERENCE TO RELATED APPLICATIONS

This is a divisional application of U.S. application Ser. No. 10/525,690, filed on Oct. 24, 2006, now U.S. Pat. No. 7,884,120, which was a U.S. national phase of International Application No. PCT/CA03/01229, filed on Aug. 19, 2003, which claimed priority from Canadian Application No. 2,398,765, filed on Aug. 19, 2002. The present application claims priority from and incorporates by reference each of the foregoing applications.

FIELD OF THE INVENTION

This invention pertains to the field of anti-microbial compounds and, in particular, to the use of 2,4,5-trisubstituted imidazole compounds in the treatment of microbial infections.

BACKGROUND OF THE INVENTION

There is currently an urgent need for compounds with broad-spectrum anti-microbial activity for the preparation of new anti-microbial agents. The increasing incidence of infectious disease caused by microbial pathogens in both communities and hospitals is a worldwide health concern. Severe invasive infections are reported as the main complication in cancer therapies, as well as bone marrow transplantation and major surgeries. Infection is also a major concern for immuno-compromised patients with haematological malignancy and/or AIDS.

Amongst bacterial pathogens, there has recently been a significant increase of multi-drug resistance. For example, strains of *Staphylococcus aureus* (methicillin-resistant or MRSA) and coagulase-negative Staphylococci (CoNS) have become resistant to the most commonly used antibiotics, such that the only available antibiotics uniformly active against them are the glycopeptides, vancomycin and teicoplanin. *S. aureus* is one of the leading causes of hospital-acquired bacteremia capable of causing a wide range of diseases ranging from superficial skin infections to potentially fatal illnesses such as bloodstream infection, endocarditis and pneumonia (Diekema et al. *Clin. Infect. Dis.* 2001, 32:S114-132). Other human pathogens that have begun to develop resistance to multiple antibiotics include *Streptococcus pneumoniae* (the leading cause of nosocomial infections) and *Pseudomonas aeruginosa*, *Haemophilus influenzae* and *Moraxella catarrhalis* (the most common community-acquired respiratory pathogens; Hoban et al. *Clin. Infect. Dis.* 2001, 32:S81-93).

Fungal infections are also becoming a major health concern for a number of reasons, including the limited number of anti-fungal agents currently available, the increasing incidence of species resistant to older anti-fungal agents, and the growing population of immuno-compromised patients at risk for opportunistic fungal infections. The most common clinical fungal isolate is *Candida albicans* (comprising about 19% of all isolates). In one study, nearly 40% of all deaths from hospital-acquired infections were due to fungi (Sternberg, *Science*, 1994, 266:1632-1634).

Thus, new classes of anti-microbial agents are needed to address both the growing resistance amongst microbes to present therapies and the general lack of efficacy of existing antibiotics against slow-growing organisms.

Heterocyclic compounds, especially heterocyclic azole derivatives, have been shown to have a wide spectrum of biological activities. One class of compounds with interesting biological activities is the imidazoles (derivatives containing a five-membered heterocyclic azole). A variety of biological activities have been reported for imidazole derivatives with different substitution patterns (Lee et al. *Nature* 1994 327: 739-745; Abdel-Meguid et al. *Biochemistry,* 1994, 33:11671; Heerding et al. *Bioorg. Med. Chem. Lett.* 2001, 11:2061-2065; Bu et al. *Tetrahedron Lett.* 1996, 37:7331-7334; Lewis J R. *Nat. Prod. Rep.* 1999, 16:389-418; Lewis J R. *Nat. Prod. Rep.* 1998, 15:417-437 and 371-395).

Biological activities have also been reported for aryl-imidazole derivatives, for example, these compounds can act as modulators of multi-drug resistance in cancer cells (Zhang et al. *Bioorg. Med. Chem. Lett.* 2000, 10:2603-2605), inhibitors of p38 MAP kinase (Adams et al. *Bioorg. Med. Chem. Lett.* 2001, 11:867-2870, McLay et. al. *Bioorg. Med. Chem.* 2001, 9:537-554) and of cytokines (U.S. Pat. Nos. 5,656,644; 5,686,455; 5,916,891; 5,945,418; and 6,268,370), and inhibitors of bacterial growth (Antolini et al. *Bioorg. Med. Chem. Lett.* 1999, 9:1023-1028).

Recent reports have indicated that triaryl-imidazole compounds can act as inhibitors of p38 MAP kinase (for example, see LoGrasso et al. *Biochemistry.* 1997, 36:10422-10427) and as modulators of multi-drug resistance in cancer cells (Sarshar et al. *Bioorg. Med. Chem. Lett.* 2000, 10:2599-2601), however, these compounds have found use mainly as colour producing reagents (U.S. Pat. Nos. 4,089,747; 5,024,935; 5,047,318; 5,496,702; 5,514,550; and 5,693,589) and as photopolymerization initiators (U.S. Pat. Nos. 6,117,609 and 6,060,216), generally in dimeric form.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide a class of compounds which are 2,4,5-trisubstituted imidazole derivatives that have anti-microbial activity. In accordance with an aspect of the present invention there is provided a use of a compound having structural formula (I), or a salt thereof, as an anti-microbial agent,

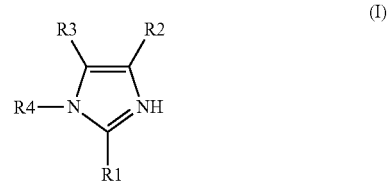

wherein:
R1 is aryl, substituted aryl, heterocycle, substituted heterocycle, heteroaryl, or substituted heteroaryl;
R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, and R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In accordance with another aspect of the present invention, there is provided a use of a compound having structural formula (I), or a salt thereof, in the treatment or prevention of a microbial infection, or a disease or disorder associated therewith, in an animal in need of such therapy.

In accordance with another aspect of the present invention, there is provided a use of a compound having structural formula (I), or a salt thereof, in the preparation of an anti-microbial composition.

In accordance with another aspect of the present invention, there is provided a method of inhibiting the growth and/or proliferation of a microbial cell comprising contacting said microbial cell with an effective amount of a compound having general formula (I), or a salt thereof.

In accordance with another aspect of the present invention, there is provided an anti-microbial composition comprising an effective amount of a compound having structural formula (I), or a salt thereof, and a carrier, diluent or excipient.

In accordance with another aspect of the present invention, there is provided a compound having the structural formula:

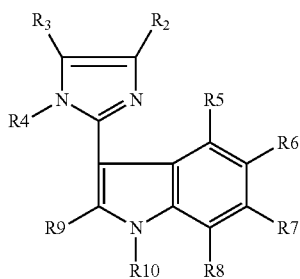

II or a salt thereof, wherein:

R2 and R3 are independently aryl, substituted aryl, heterocycle, heteroaryl, substituted heterocycle, or substituted heteroaryl or R2 and R3 when taken together along with the carbon atoms they are attached form aryl or substituted aryl, heterocycle, heteroaryl, substituted heterocycle, or substituted heteroaryl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, or —CH$_2$-heteroaryl.

In accordance with another aspect of the present invention, there is provided a compound having the structural formula:

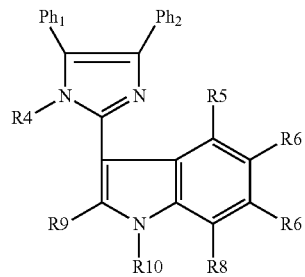

III or a salt thereof, wherein:

Ph1 and Ph2 are independently selected from phenyl and substituted phenyl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, or —CH$_2$-heteroaryl;

with the proviso that the compounds are other than:

3-(4,5-diphenyl-1H-imidazol-2-yl)-1-methyl-1H-indole;

3-[4-(4-chlorophenyl)-5-phenyl-1H-imidazol-2-yl]-1-methyl-1H-indole;

3-[4-(4-bromophenyl)-5-phenyl-1H-imidazol-2-yl]-1-methyl-1H-indole;

3-[4-(4-methylphenyl)-5-phenyl-1H-imidazol-2-yl]-1-methyl-1H-indole;

3-[4-(4-methoxyphenyl)-5-phenyl-1H-imidazol-2-yl]-1-methyl-1H-indole;

3-[4-(4-ethoxyphenyl)-5-phenyl-1H-imidazol-2-yl]-1-methyl-1H-indole;

3-[4,5-bis(4-methoxydiphenyl)-1H-imidazol-2-yl]-1-methyl-1H-indole;

4,4'-[2-(2-phenyl-1H-indol-3-yl)-1H-imidazole-4,5-diyl]bis[N,N-dimethyl]benzenamine;

4,4'-[2-(5-chloro-1H-indol-3-yl)-1H-imidazole-4,5-diyl]bis[N,N-dimethyl]benzenamine;

2-(3-indolyl)-4,5-bis[4-(dimethylamino)phenyl]imidazole;

2-(3-indolyl)-4,5-bis[4-(diethylamino)phenyl]imidazole;

2-(2-phenyl-3-indolyl)-4,5-bis[4-(dimethylamino)phenyl]imidazole;

2-(2-chloro-3-indolyl)-4,5-bis[4-(dimethylamino)phenyl]imidazole;

2-(2-ethylcarboxylate-3-indolyl)-4,5-bis[4-(dimethylamino)phenyl]imidazole;

2-(5-chloro-3-indolyl)-4,5-bis[4-(dimethylamino)phenyl]imidazole;

2-(5-cyano-3-indolyl)-4,5-bis[4-(dimethylamino)phenyl]imidazole;

2-(5-nitro-3-indolyl)-4,5-bis[4-(dimethylamino)phenyl]imidazole.

In accordance with another aspect of the present invention, there is provided a compound having the structural formula:

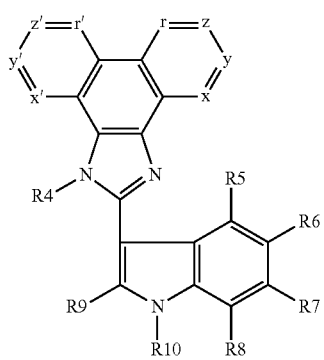

or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;
R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, or —CH$_2$-heteroaryl;
x is CR11 or N;
y is CR12 or N;
z is CR13 or N;
r is CR14 or N;
x' is CR15 or N;
y' is CR16 or N;
z' is CR17 or N;
r' is CR18 or N;
R11, R12, R13, R14, R15, R16, R17 and R18 are independently selected from hydrogen, halogen, hydroxyl, thiol, lower alkyl, substituted lower alkyl, alkenyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In accordance with another aspect of the present invention, there is provided a compound having the structural formula:

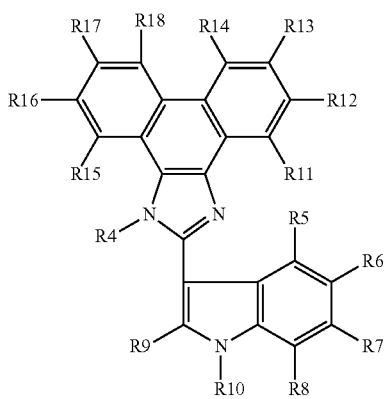

or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;
R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, or —CH$_2$-heteroaryl;
R11, R12, R13, R14, R15, R16, R17 and R18 are independently selected from hydrogen, halogen, hydroxyl, thiol, lower alkyl, substituted lower alkyl, alkenyl, alkenyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

BRIEF DESCRIPTION OF THE FIGURES

FIG. 1 depicts the bactericidal effect of compounds of Formula I against multi-drug resistant *Staphylococcus aureus* (CMRSA-1B).

DETAILED DESCRIPTION OF THE INVENTION

The present invention provides a class of 2,4,5-trisubstituted imidazole compounds and for their use as anti-microbial agents. In the context of the present invention, the term "anti-microbial" refers to the inhibition, prevention or eradication of the growth or proliferation of bacteria and/or fungi and to the inhibition, prevention or eradication of the growth or proliferation of microbially-infected cells.

Definitions

Unless defined otherwise, all technical and scientific terms used herein have the same meaning as commonly understood by one of ordinary skill in the art to which this invention pertains.

The terms are defined as follows:

The term "halogen" refers to fluorine, bromine, chlorine, and iodine atoms.

The term "hydroxyl" refers to the group —OH.

The term "thiol" or "mercapto" refers to the group —SH, and —S(O)$_{0-2}$.

The term "lower alkyl" refers to a straight chain or branched, or cyclic, alkyl group of one to ten carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, hexyl and the like.

The term "substituted lower alkyl" refers to lower alkyl as just described including one or more groups such as hydroxyl, thiol, alkylthio, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, cyano. These groups may be attached to any carbon atom of the lower alkyl moiety.

The term "lower alkenyl" refers to a straight chain or branched, alkenyl group of two to ten carbon atoms.

The term "substituted lower alkenyl" refers to lower alkenyl as just described including one or more groups such as hydroxyl, thiol, alkylthio, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl, alkenyl, alkynyl, alkyl alkenyl, alkyl alkynyl, alkyl cycloalkyl, alkyl cycloheteroalkyl, cyano. These groups may be attached to any carbon atom of the lower alkyl moiety.

The term "alkenyl" refers to a group —CR'=CR"R'" where R', R", R'" are each independently selected from hydrogen, halogen, lower alkyl, substituted lower alkyl, acyl, aryl, substituted aryl, heteroaryl, substituted heteroaryl or the like as defined.

The term "lower alkynyl" refers to a straight chain or branched, alkynyl group of two to ten carbon atoms.

The term "substituted lower alkynyl" refers to lower alkynyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl, alkenyl, alkynyl, alkyl alkenyl, alkyl alkynyl, alkyl cycloalkyl, alkyl cycloheteroalkyl, cyano. These groups may be attached to any carbon atom of the lower alkyl moiety.

The term "alkynyl" refers to a group —C≡C—R'; where R' is selected from hydrogen, halogen, lower alkyl, substituted lower alkyl, acyl, aryl, substituted aryl, heteroaryl, substituted heteroaryl or the like as defined.

The term "alkyl alkenyl" refers to a group —R—CR'=CR'"R"", where R is lower alkyl, or substituted lower alkyl, —(CR'=CR")$_n$— or —(C≡C)$_n$—, wherein n is 1-8, R'", R"" are each independently selected from hydrogen, halogen, lower alkyl, substituted lower alkyl, acyl, aryl, substituted aryl, hetaryl, or substituted hetaryl as defined below.

The term "alkyl alkynyl" refers to a group —R—C≡CR' where R is lower alkyl or substituted lower alkyl, R' is hydrogen, lower alkyl, substituted lower alkyl, acyl, aryl, substituted aryl, hetaryl, or substituted hetaryl as defined below.

The term "alkoxy" refers to the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined below.

The term "alkylthio" denotes the group —SR, —S(O)$_{n=1-2}$—R, where R is lower alkyl, substituted lower alkyl, aryl, substituted aryl, aralkyl or substituted aralkyl as defined below.

The term "acyl" refers to groups —C(O)R, where R is hydrogen, lower alkyl, substituted lower alkyl, aryl, substituted aryl.

The term "aryloxy" refers to groups —OAr, where Ar is an aryl, substituted aryl, heteroaryl, or substituted heteroaryl group as defined below.

The term "amino" refers to the group NRR', where R and R' may independently be hydrogen, lower alkyl, substituted lower alkyl, aryl, substituted aryl, hetaryl, cycloalkyl, or substituted hetaryl as defined below or acyl.

The term "amido" refers to the group —C(O)NRR', where R and R' may independently be hydrogen, lower alkyl, substituted lower alkyl, aryl, substituted aryl, hetaryl, substituted hetaryl as defined below.

The term "carboxyl" refers to the group —C(O)OR, where R may independently be hydrogen, lower alkyl, substituted lower alkyl, aryl, substituted aryl, hetaryl, substituted hetaryl and the like as defined.

The terms "aryl" or "Ar" refer to an aromatic carbocyclic group having at least one aromatic ring (e.g., phenyl or biphenyl) or multiple condensed rings in which at least one ring is aromatic (e.g., 1,2,3,4-tetrahydronaphthyl, naphthyl, anthryl, or phenanthryl, 9-fluorenyl etc.).

The term "substituted aryl" refers to aryl optionally substituted with one or more functional groups, e.g., halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl, indanyl or benzo[b]thienyl) and having at least one hetero atom, such as N, O or S, within the ring.

The term "substituted heterocycle" refers to heterocycle optionally substituted with, halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano and the like.

The terms "heteroaryl" or "hetaryl" refer to a heterocycle in which at least one heterocyclic ring is aromatic.

The term "substituted heteroaryl" refers to a heterocycle optionally mono or poly substituted with one or more functional groups, e.g., halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano and the like.

The term "aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkyl thio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, aryl, aryloxy, heterocycle, hetaryl, substituted hetaryl, nitro, cyano, alkylthio, thiol, sulfamido and the like.

The term "cycloalkyl" refers to a cyclic or polycyclic alkyl group containing 3 to 15 carbon. For polycyclic groups, these may be multiple condensed rings in which one of the distal rings may be aromatic (e.g. tetrahydronaphthalene, etc.).

The term "substituted cycloalkyl" refers to a cycloalkyl group comprising one or more substituents with, e.g halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, sulfamido or cyano and the like.

The term "cycloheteroalkyl" refers to a cycloalkyl group wherein one or more of the ring carbon atoms is replaced with a heteroatom (e.g., N, O, S or P).

The term "substituted cycloheteroalkyl" refers to a cycloheteroalkyl group as herein defined which contains one or more substituents, such as halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "alkyl cycloalkyl" refers to the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

I. 2,4,5-Trisubstituted Imidazole Compounds

The present invention provides compounds of the general formula (I):

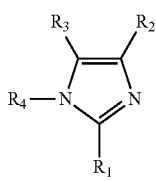

or a salt thereof, wherein:

R1 is aryl, substituted aryl, heterocycle, substituted heterocycle, heteroaryl, or substituted heteroaryl;

R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, heterocycle, substituted heterocycle, heteroaryl, or substituted heteroaryl;

R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I

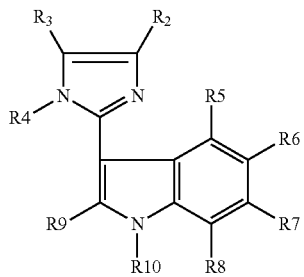

include the compound of the structural formula:
or a salt thereof, wherein:

R2 and R3 are independently aryl, substituted aryl, heterocycle, heteroaryl, substituted heterocycle, or substituted heteroaryl or R2 and R3 when taken together along with the carbon atoms they are attached form aryl or substituted aryl, heterocycle, heteroaryl, substituted heterocycle, or substituted heteroaryl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, or —CH$_2$-heteroaryl.

In another embodiment the compound of formula II is other than 3,3'-[5-(4-methoxyphenyl)-1H-imidazole-2,4-diyl]bis-1H-indole.

In another embodiment of the present invention, in the compound of formula II, when R2 is selected from phenyl and substituted phenyl then R3 is selected from heterocycle, heteroaryl, substituted heterocycle, or substituted heteroaryl, aryl other than phenyl and substituted aryl other than substituted phenyl or vice versa.

In another embodiment of the present invention, in the compound of formula II, when R2 is selected from phenyl and substituted phenyl then R3 is selected from heterocycle, heteroaryl, substituted heterocycle, or substituted heteroaryl or vice versa.

In another embodiment of the present invention, in the compound of formula II, when R2 and R3 are independently selected from phenyl and substituted phenyl, then, i) R2 and R3 are not phenyl at the same time; or ii) R2 and R3 do not have the same substituents on the same position.

In another embodiment of the present invention, in the compound of formula II, when R2 is selected from phenyl and phenyl substituted with halo, alkyl or alkoxy then R3 is selected from a phenyl substituted with a substitutent other than halo, alkyl or alkoxy.

In another embodiment of the present invention, the compound of Formula II includes the compound of the structural formula III:

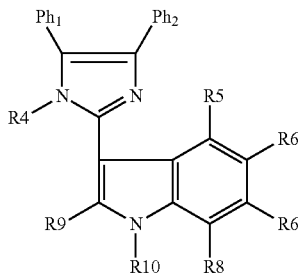

III

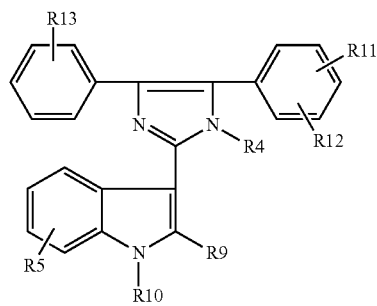

IV or a salt thereof, wherein:

Ph1 and Ph2 are independently selected from phenyl and substituted phenyl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, or acyl.

with the proviso that the compounds are other than:

3-(4,5-diphenyl-1H-imidazol-2-yl)-1-methyl-1H-indole;

3-[4-(4-chlorophenyl)-5-phenyl-1H-imidazol-2-yl]-1-methyl-1H-indole;

3-[4-(4-bromophenyl)-5-phenyl-1H-imidazol-2-yl]-1-methyl-1H-indole;

3-[4-(4-methylphenyl)-5-phenyl-1H-imidazol-2-yl]-1-methyl-1H-indole;

3-[4-(4-methoxyphenyl)-5-phenyl-1H-imidazol-2-yl]-1-methyl-1H-indole;

3-[4-(4-ethoxyphenyl)-5-phenyl-1H-imidazol-2-yl]-1-methyl-1H-indole;

3-[4,5-bis(4-methoxydiphenyl)-1H-imidazol-2-yl]-1-methyl-1H-indole;

4,4'-[2-(2-phenyl-1H-indol-3-yl)-1H-imidazole-4,5-diyl]bis[N,N-dimethyl]benzenamine;

4,4'-[2-(5-chloro-1H-indol-3-yl)-1H-imidazole-4,5-diyl]bis[N,N-dimethyl]benzenamine;

2-(3-indolyl)-4,5-bis[4-(dimethylamino)phenyl]imidazole;

2-(3-indolyl)-4,5-bis[4-(diethylamino)phenyl]imidazole;

2-(2-phenyl-3-indolyl)-4,5-bis[4-(dimethylamino)phenyl]imidazole;

2-(2-chloro-3-indolyl)-4,5-bis[4-(dimethylamino)phenyl]imidazole;

2-(2-ethylcarboxylate-3-indolyl)-4,5-bis[4-(dimethylamino)phenyl]imidazole;

2-(5-chloro-3-indolyl)-4,5-bis[4-(dimethylamino)phenyl]imidazole;

2-(5-cyano-3-indolyl)-4,5-bis[4-(dimethylamino)phenyl]imidazole;

2-(5-nitro-3-indolyl)-4,5-bis[4-(dimethylamino)phenyl]imidazole;

In another embodiment of the invention, the compound of Formula III is selected from:

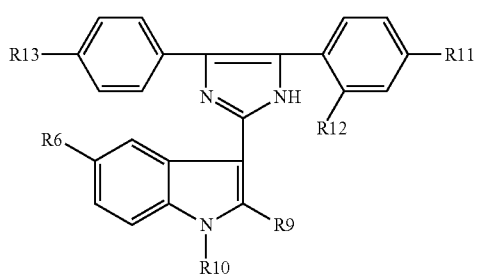

V or a salt thereof, wherein:

R5, R6, R9, R11, R12 and R13 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, or acyl.

In another embodiment of the present invention, the compound of Formula I includes the compound of the structural formula:

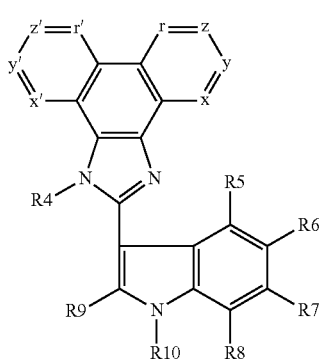

VI or a salt thereof, wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

x is CR11 or N;
y is CR12 or N;
z is CR13 or N;
r is CR14 or N;
x' is CR15 or N;
y' is CR16 or N;
z' is CR17 or N;
r' is CR18 or N;
R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I includes the compound of the structural formula:

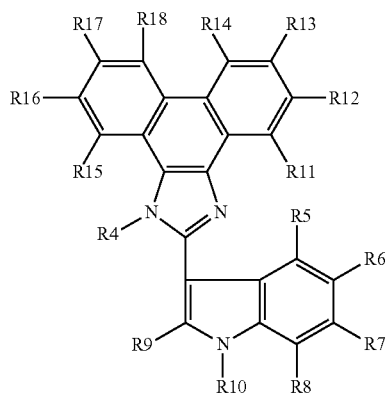

VII or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;
R10 is H, alkyl, substituted alkyl, alkenyl, substituted alkenyl, alkynyl, substituted alkynyl, aryl, substituted aryl, heteroaryl, substituted heteroaryl, or acyl;
R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I is selected from the compound of formula:

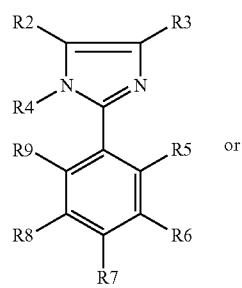

VIII or

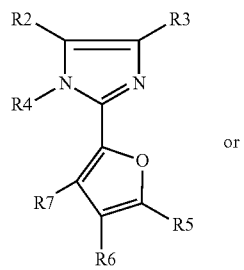

IX or

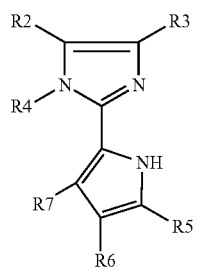

X wherein:
R2 and R3 are independently aryl, substituted aryl, heterocycle, heteroaryl, substituted heterocycle, or substituted heteroaryl or R2 and R3 when taken together along with the carbon atoms they are attached to, form a aryl, substituted aryl, heterocycle, heteroaryl, substituted heterocycle, or substituted heteroaryl;
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I includes the compound of the structural formula:

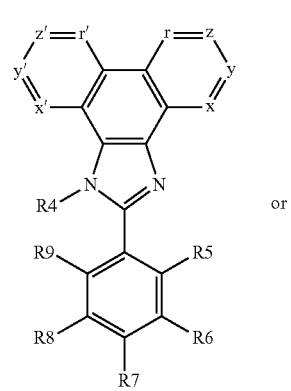

XI or

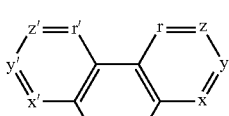
XII or

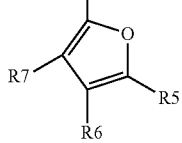
XIII

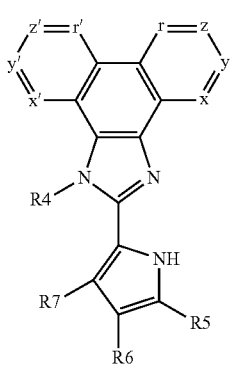

or a salt thereof, wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

x is CR11 or N;

y is CR12 or N;

z is CR13 or N;

r is CR14 or N;

x' is CR15 or N;

y' is CR16 or N;

z' is CR17 or N;

r' is CR18 or N;

R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the invention, the compound of Formula I is selected from:

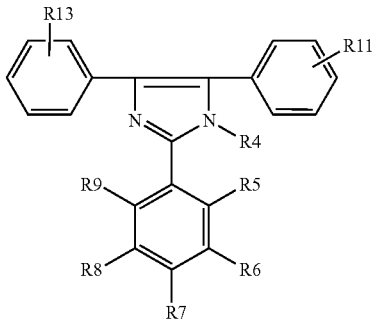
XIV

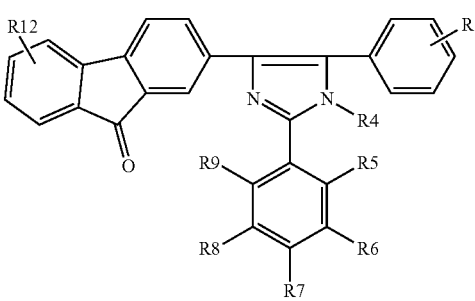
XV

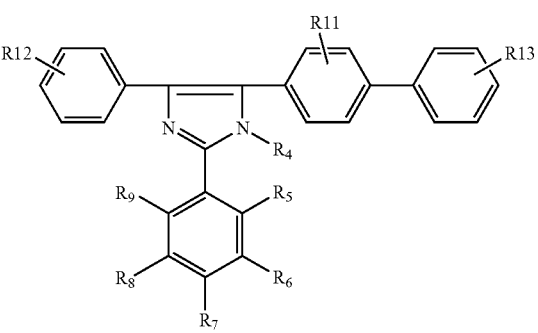
XVI

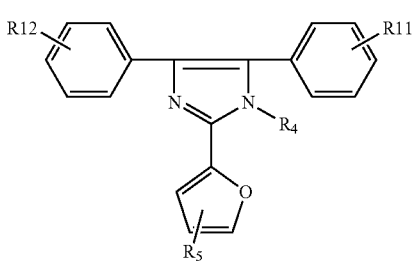
XVII wherein:

R4, R5, R6, R7, R8, R9, R11, R12 and R13 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the invention the compound of Formula I is selected from:

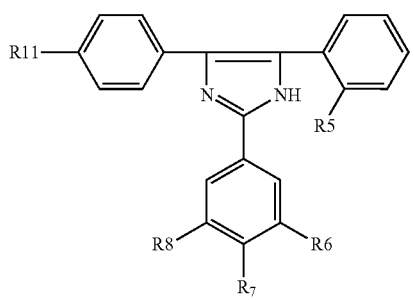

XVIII

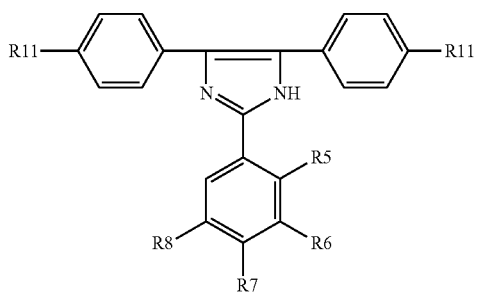

XIX

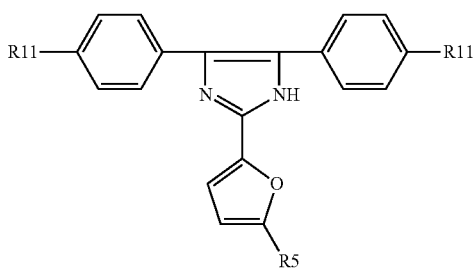

XX

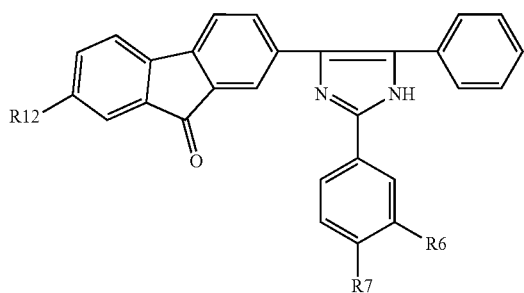

XXI

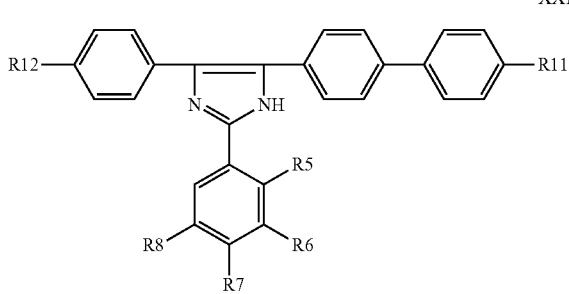

XXII

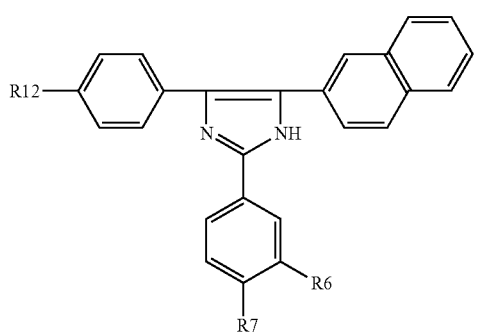

XXIII wherein:

R5, R6, R7, R8, R11 and R12 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

Compounds of the present invention include, but are not limited to the following exemplary compounds:

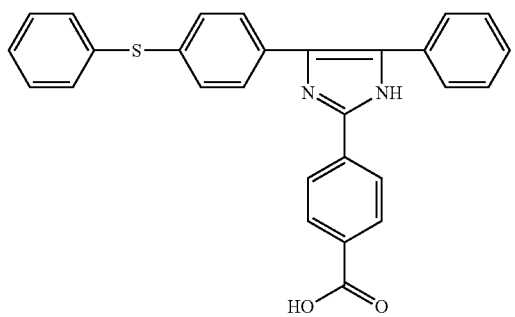 [SMILES: O=C(O)c1ccc(-c2nc(-c3ccc(Sc4ccccc4)cc3)c(-c3ccccc3)[nH]2)cc1]

1

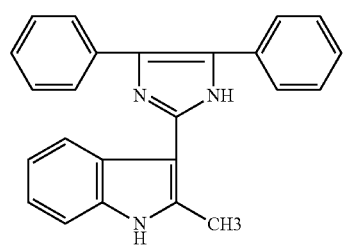 [SMILES: Cc1[nH]c2ccccc2c1-c1nc(-c2ccccc2)c(-c2ccccc2)[nH]1]

2

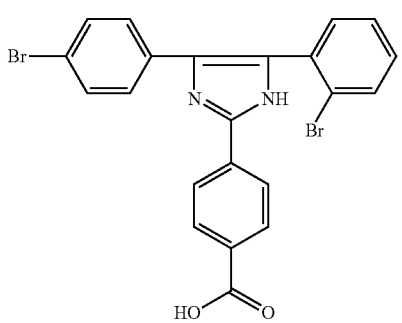 [SMILES: O=C(O)c1ccc(-c2nc(-c3ccc(Br)cc3)c(-c3ccccc3Br)[nH]2)cc1]

3

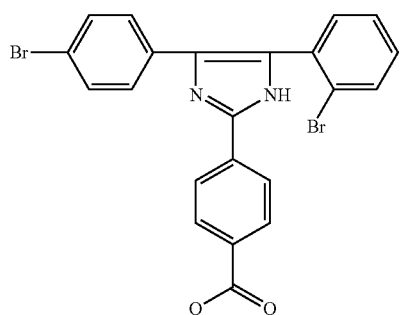 [SMILES: O=C(O)c1ccc(-c2nc(-c3ccc(Br)cc3)c(-c3ccccc3Br)[nH]2)cc1]
4
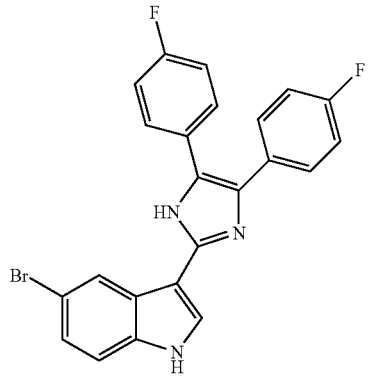
8
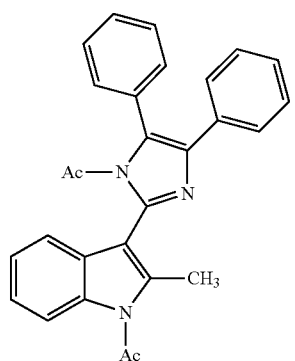
5
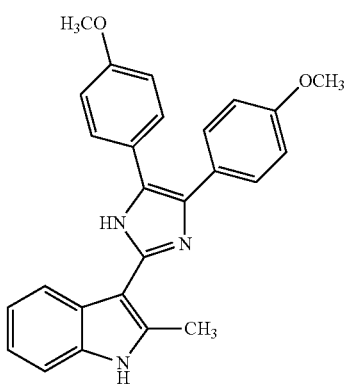
9
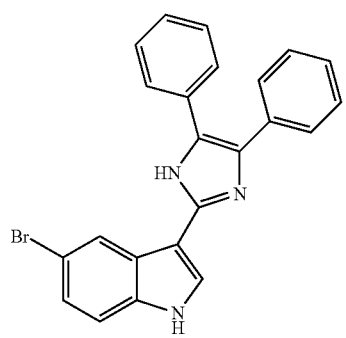
6
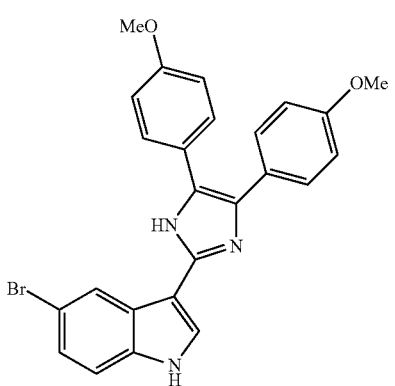
10
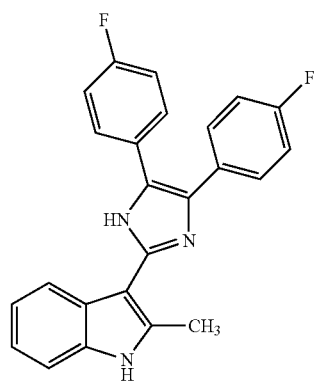
7
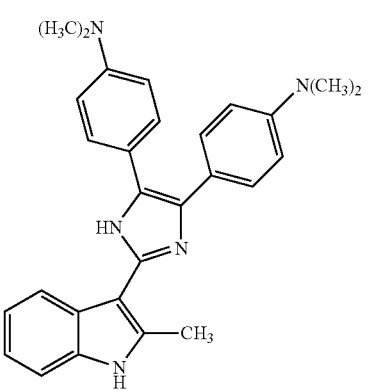
11

12
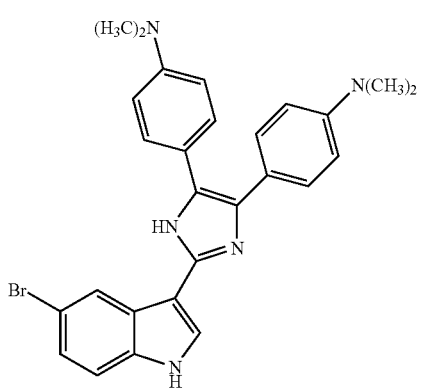
13
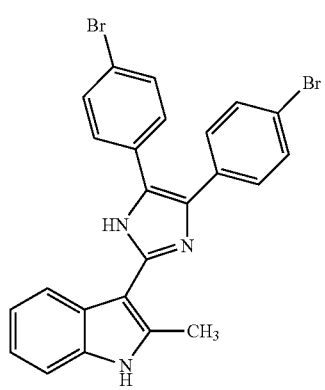
14
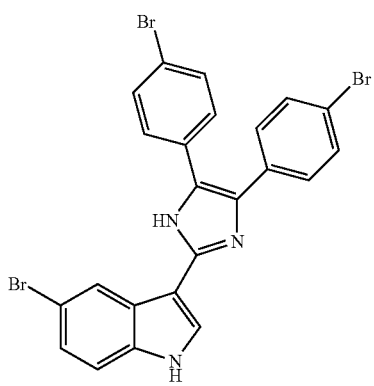
15
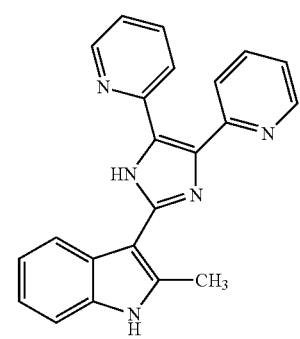
16
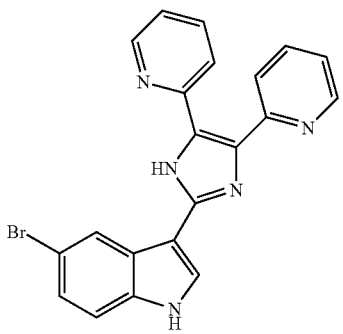
17
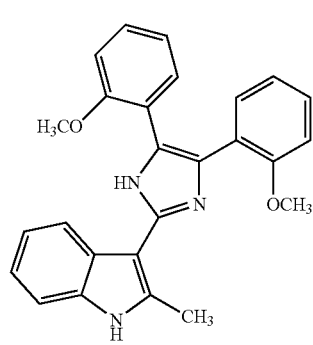
18
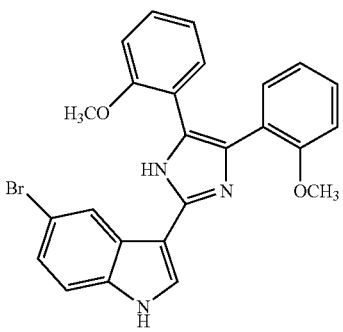
19
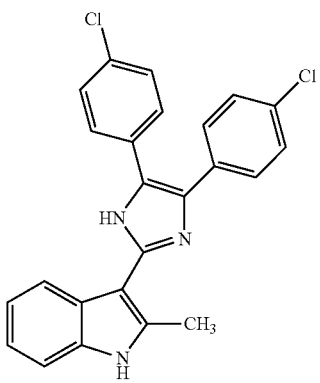

20
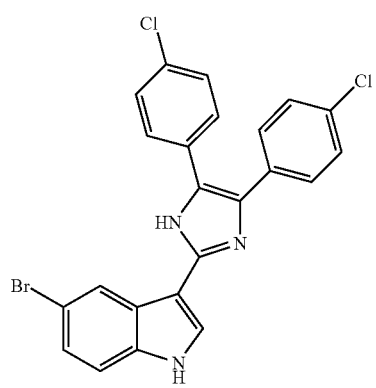
21
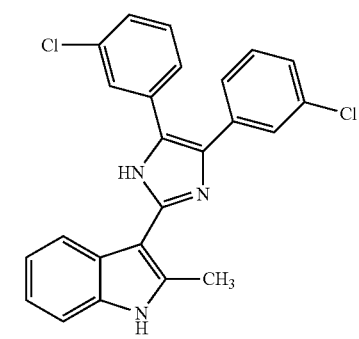
22
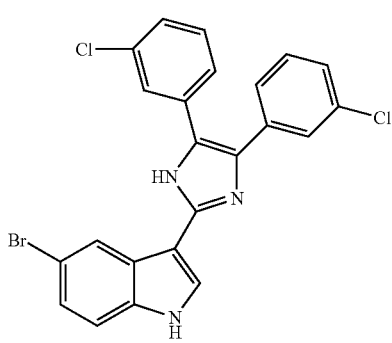
23
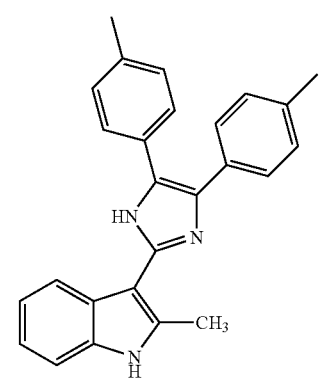
24
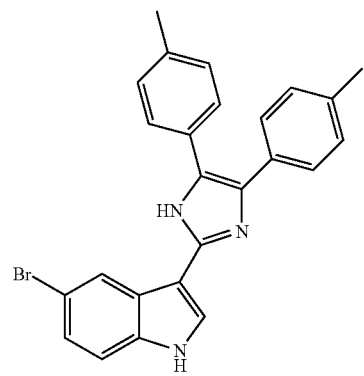
25
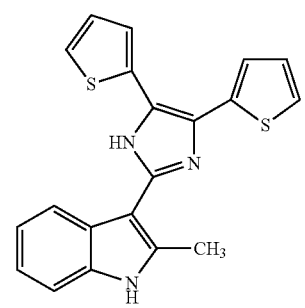
26
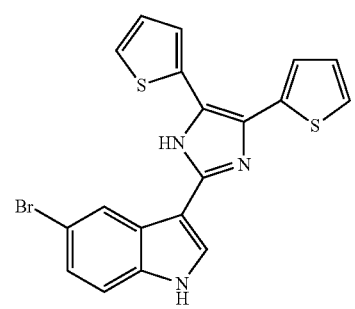
27
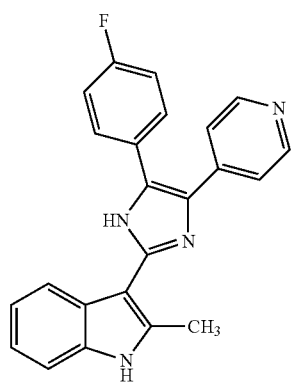

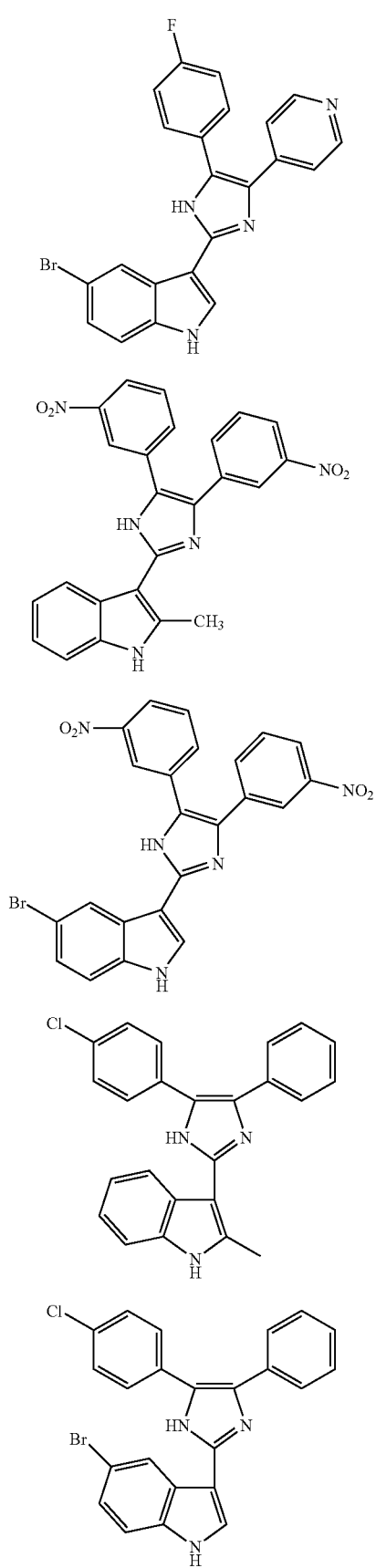
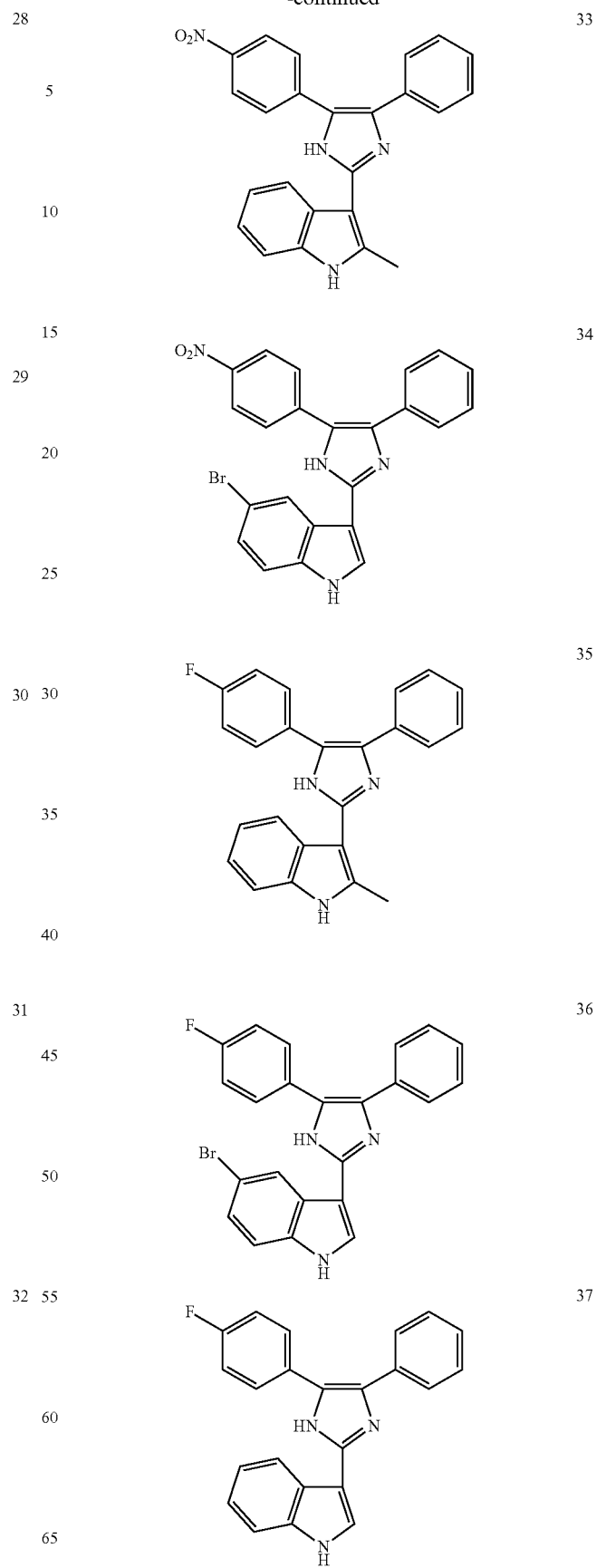

-continued
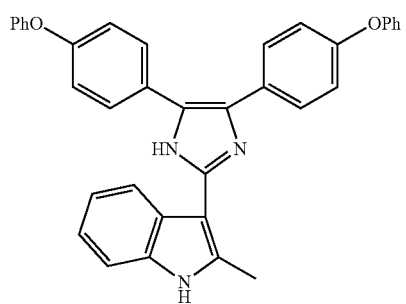
38
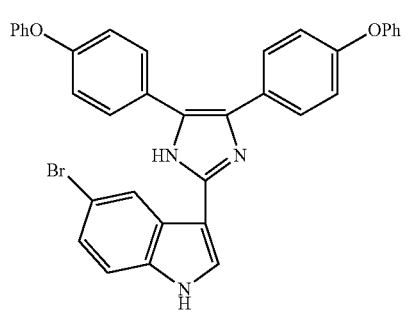
39
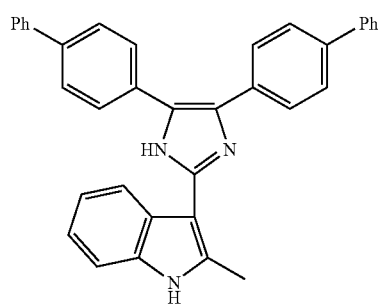
40
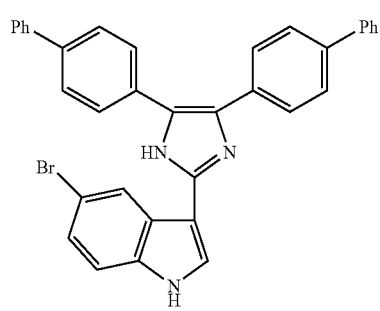
41
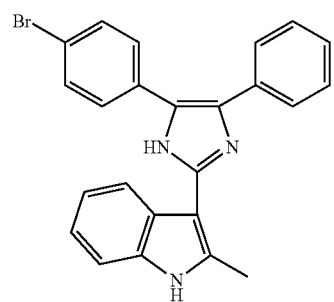
42
-continued
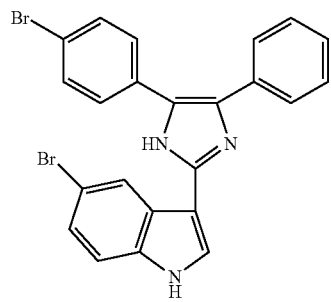
43
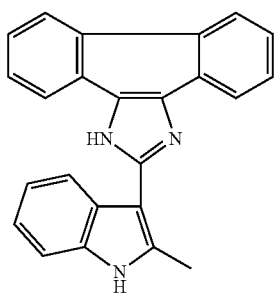
44
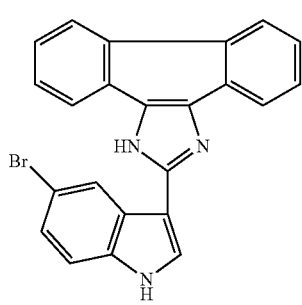
45
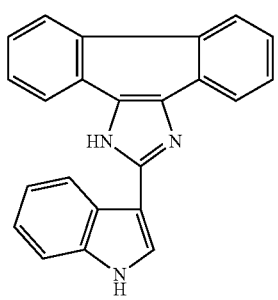
46
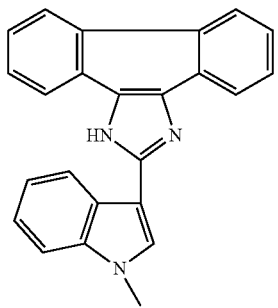
47

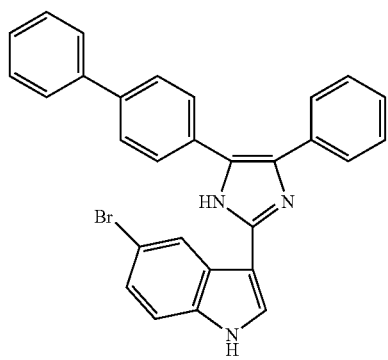
48
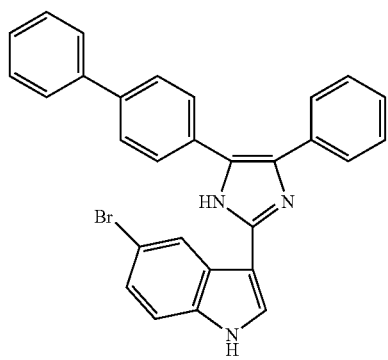
49
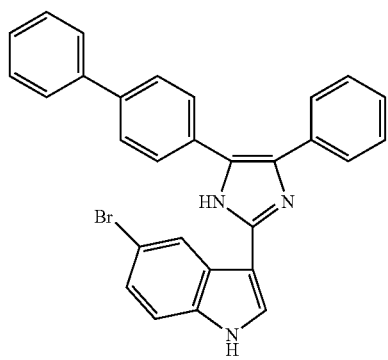
50
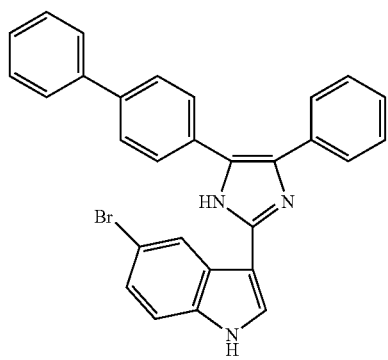
51
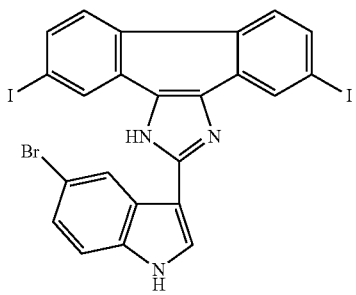
52
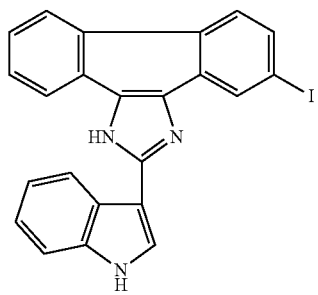
53
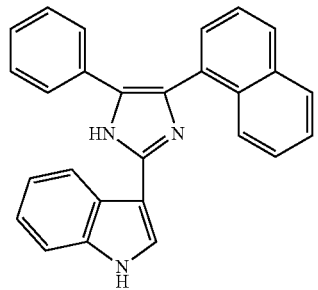
54
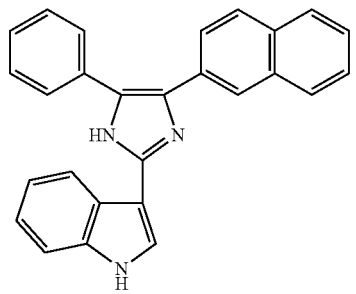
55
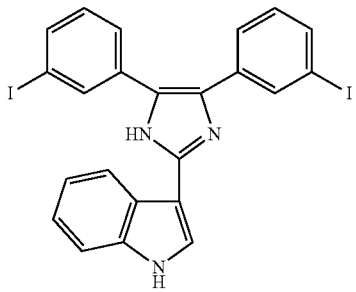
56

57
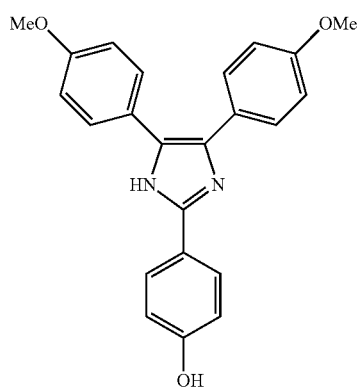
58
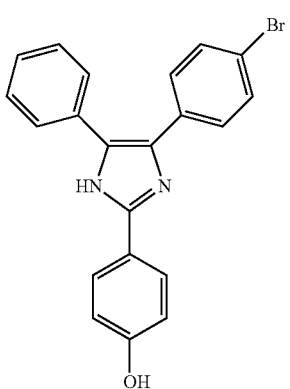
59
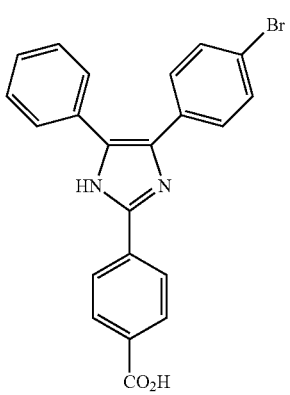
60
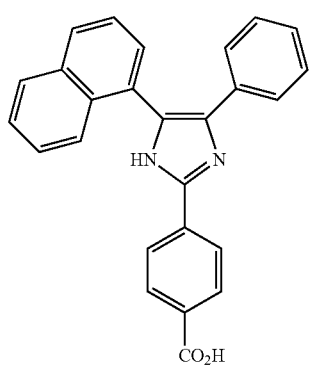
61
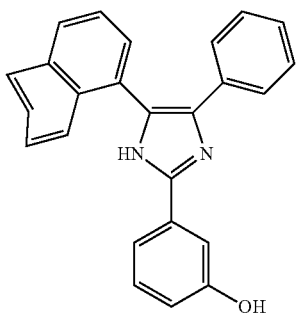
62
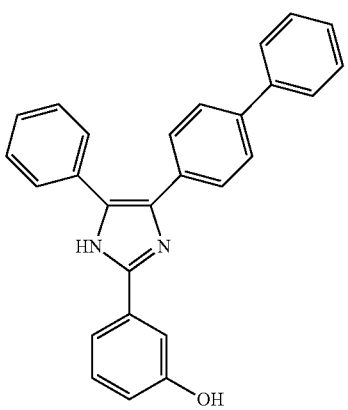
63
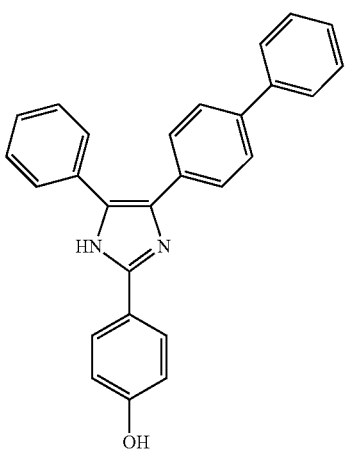
64
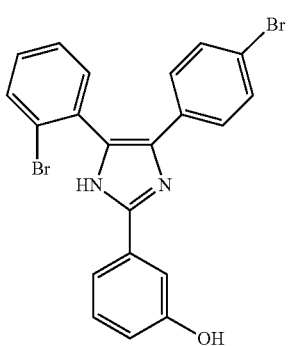

65
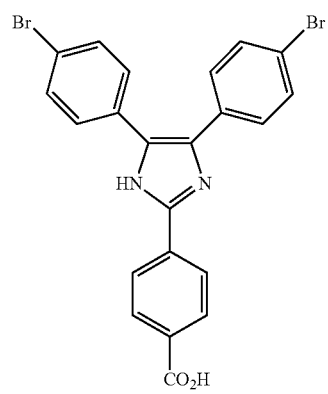
66
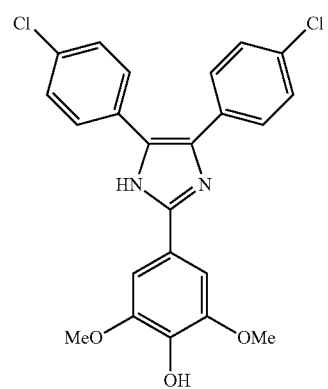
67
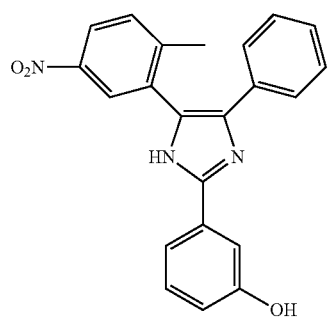
68
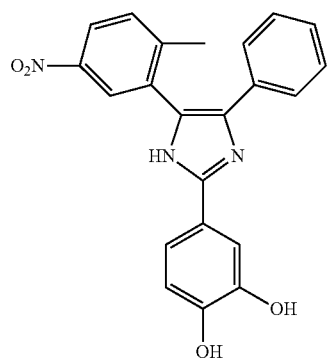
69
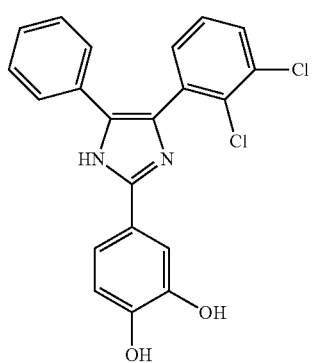
70
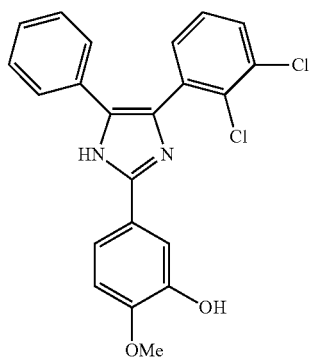
71
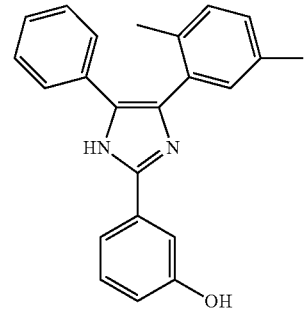
72
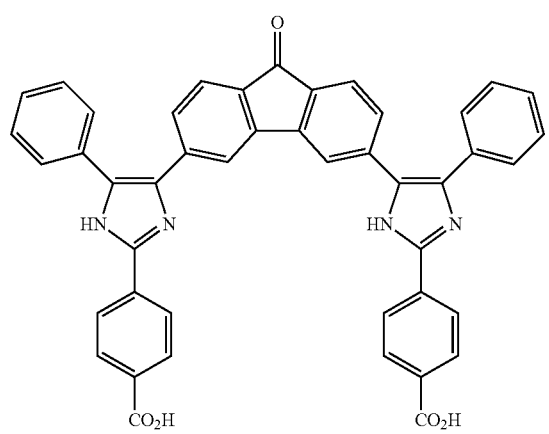

-continued
73
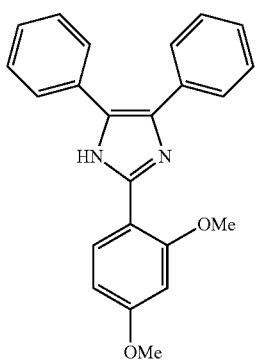
74
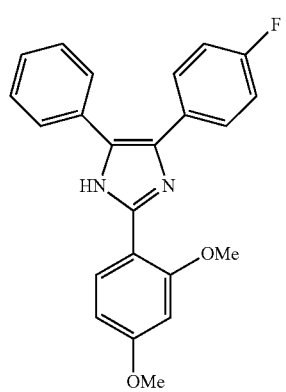
75
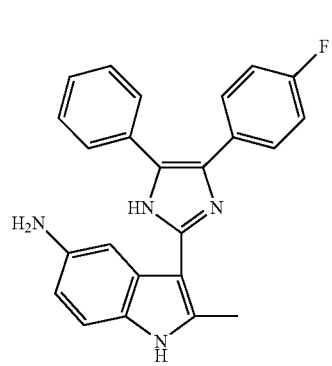
76
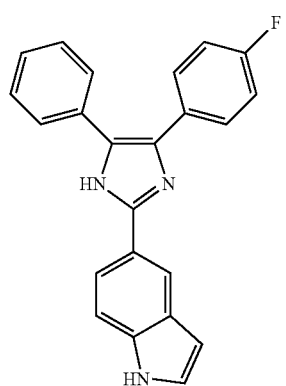
-continued
77
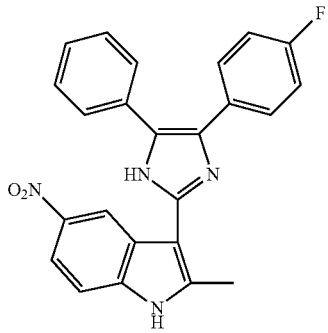
78
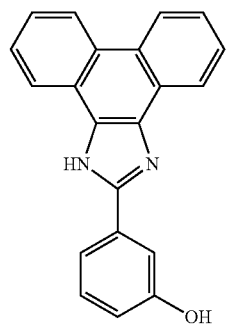
79
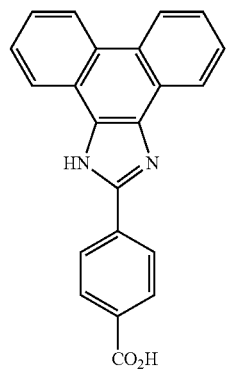
80
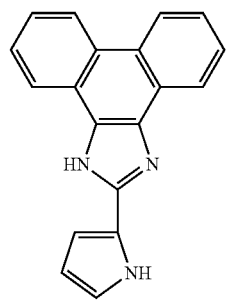

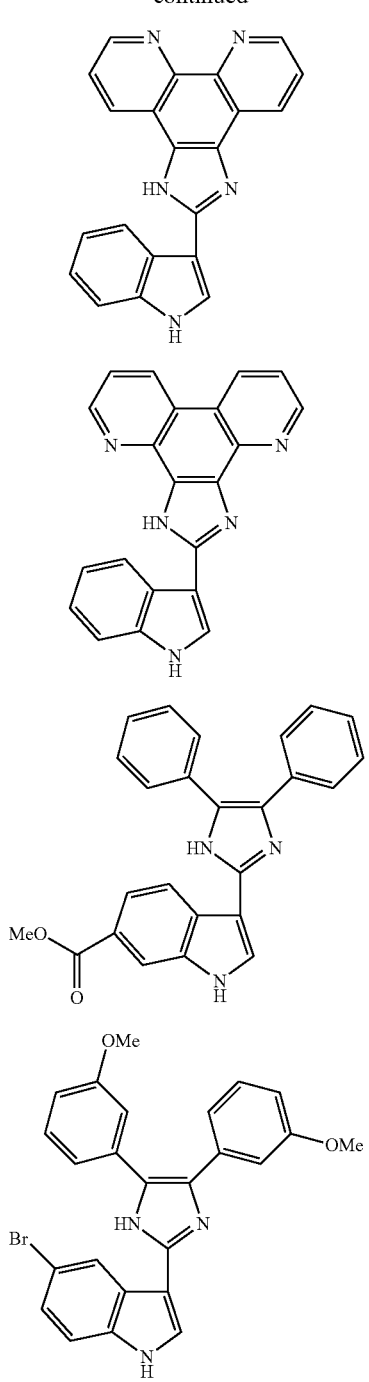

The present invention includes pharmaceutically acceptable salts of the compounds defined by Formula I. Compounds according to the present invention can possess a sufficiently acidic, a sufficiently basic, or both functional groups, and accordingly react with a number of organic and inorganic bases, and organic and inorganic acids, to form pharmaceutically acceptable salts.

The term "pharmaceutically acceptable salt" as used herein, refers to a salt of a compound of Formula I, which is substantially non-toxic to living organisms. Typical pharmaceutically acceptable salts include those salts prepared by reaction of the compound of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulphonic acid.

Salts of amine groups may also comprise quaternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a salt of this invention is usually not of a critical nature, so long as the salt as a whole is pharmacologically acceptable and as long as the counterion does not contribute undesired qualities to the salt as a whole. The present invention further encompasses the pharmaceutically acceptable solvates of a compound of Formula I. Many of the compounds of Formula I can combine with solvents such as water, methanol, ethanol and acetonitrile to form pharmaceutically acceptable solvates such as the corresponding hydrate, methanolate, ethanolate and acetonitrilate.

The compounds of the present invention may have multiple asymmetric (chiral) centres. As a consequence of these chiral centres, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

It will be readily understood by one skilled in the art that if the stereochemistry of a compound of Formula I is critical to its activity, then the relative stereochemistry of the compound is established early during synthesis to avoid subsequent stereoisomer separation problems. Further manipulation of the molecule will then employ stereospecific procedures so as to maintain the desired chirality.

Non-toxic metabolically-labile esters or amides of a compound of Formula I are those that are hydrolysed in vivo to afford the compound of Formula I and a pharmaceutically acceptable alcohol or amine. Examples of metabolically-labile esters include esters formed with (1-6C) alkanols, in which the alkanol moiety may be optionally substituted by a (1-8C) alkoxy group, for example methanol, ethanol, propanol and methoxyethanol. Examples of metabolically-labile amides include amides formed with amines such as methylamine.

II. Preparation of Compounds of Formula I

As is known in the art, triaryl imidazole compounds can be prepared by a number of standard techniques. Compounds of Formula I, therefore, can be prepared by several general synthetic methods, for example, as described by Grimmett, (Grimmett, M. R., *Comprehensive Heterocyclic Chemistry: The Structure, Reaction, Synthesis and Uses of Heterocyclic Compounds*, A. R. Katrizky and C. W. Rees, eds., Vol. 5, Pergamon Press. Oxford, 1984, pp. 457-498; Grimmett, M. R., *Imidazole and Benzimidazole Synthesis*, Academic Press, San Diego Calif., 1997).

In one embodiment of the present invention, compounds of Formula I are prepared via solution or solid phase synthesis, by reacting a dione of Formula II with the aldehyde (III) at elevated temperature in the presence of ammonium acetate in acetic acid (see, for example, Krieg et al., *Naturforsch.* 1967, 22b:132; Sarshar et al., *Tetrahedron Lett.* 1996, 37:835-838).

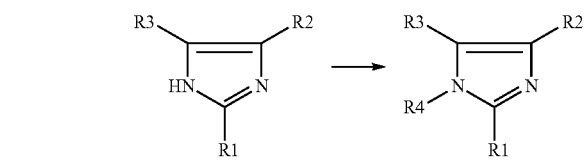

The compounds of Formula (II) and (III) are either commercially available or may be prepared using standard procedures known to a person skilled in the relevant art. Compounds of Formula II, therefore, can be prepared by several general synthetic methods, for example, as described by: Fischer et. al (*J. Am. Chem. Soc.* 1961, 83, 4208-4210); Guijarro et al. (*J. Am. Chem. Soc.* 1999, 121, 4155-4157); Chi et. al. (*Synth. Comm.* 1994, 24(15), 2119-2122) and Armesto et. al. (*Synthesis*, 1988, 799-801).

Compounds of formula II can also be prepared:

i) by oxidizing a compound of formula (IV). Compounds of formula (IV), in turn can be prepared by reacting a compounds of formula (V) with sodium cyanide in the presence of a solvent as shown below, wherein R2 is as defined above:

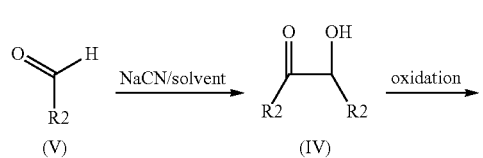

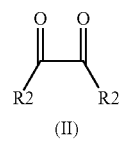

or, ii) by oxidizing a compound of formula (VI). Compounds of formula (VI), in turn can be prepared by treating a compound of formula (V) and a compound of formula (VII) with sodium cyanide in the presence of a solvent as shown below, wherein R2 and R3 are as defined above:

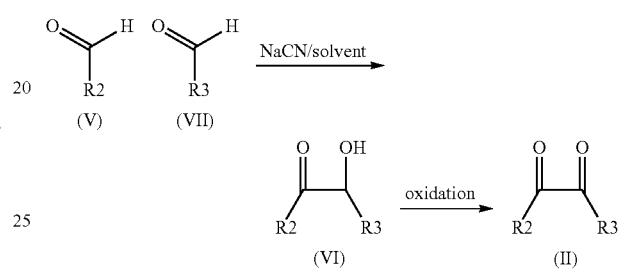

or, iii) by oxidizing a compound of formula (VIII). Compounds of formula (VIII) in turn can be prepared by oxidizing a compound of formula (IX) or (X) as shown below, wherein R2 and R3 are as defined above:

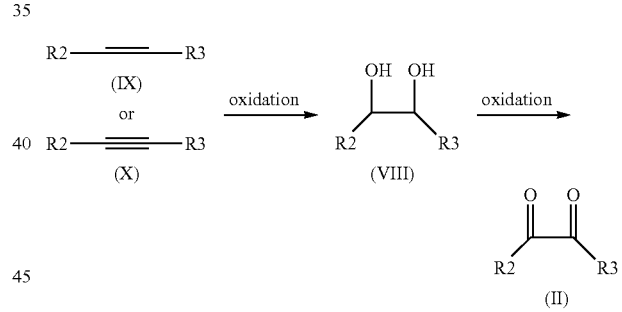

or, iv) by oxidizing a compound of formula (X) using PdCl$_2$ in DMSO, or, v) by deprotecting and oxidizing a compound of formula (XI). Compounds of formula (XI) in turn can be prepared by reacting a compound of formula (XII) with a compound of formula (XIII) in the presence of a suitable base:

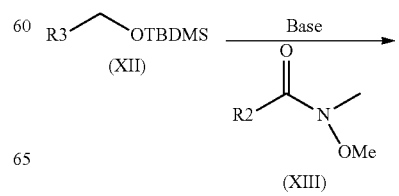

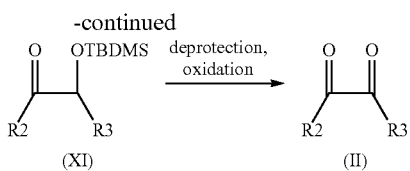

wherein R2 and R3 are independently aryl, substituted aryl, heteroaryl or substituted heteroaryl,
or,
vi) by reacting a compound of formula (XIV) with a substituted or unsubstituted aryl or substituted or unsubstituted heteroaryl under Friedel Crafts acylation conditions or by nuecleophilic displacement of the chloride in compound of formula XIV. Compounds of formula (XIV) in turn can be prepared by reacting a substituted or unsubstituted aryl or substituted or unsubstituted heteroaryl with oxalyl chloride under Friedel Crafts acylation conditions:

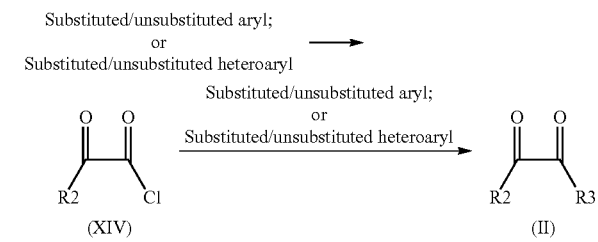

wherein R2 and R3 are independently aryl, substituted aryl, heteroaryl or substituted heteroaryl;
or
vii) by oxidising a compound of formula (XV). Compounds of formula (XV) in turn is prepared by reacting a compound of formula (XVI) with thionyl chloride in benzene with catalytic dimethylformamide to form an intermediate (XVII). This intermediate (XVII) is then used directly without purification in a freidel-Crafts reaction to produce the Ketone (XV).

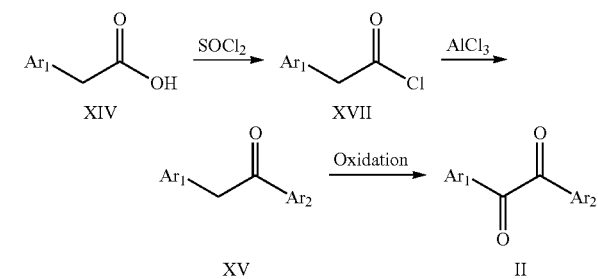

III. Anti-Microbial Activity of Compounds of Formula I

The anti-microbial activity of a candidate compound of Formula I can be tested using standard techniques known in the art. In accordance with the present invention, the anti-microbial activity exhibited by a candidate compound may be anti-bacterial activity, anti-fungal activity, or both anti-bacterial and anti-fungal activity. As is known in the art, anti-microbial activity of a compound may result in the killing of microbial cells (i.e. bacteriocidal and/or fungicidal activity), or it may result in the slowing or arrest of the growth of microbial cells (i.e. bacteriostatic or fungistatic activity). Thus the compounds of Formula I may be bacteriocidal and/or fungicidal or they may be bacteriostatic and/or fungistatic. Compounds of the present invention that slow or arrest microbial cell growth may be useful in combination treatments with other known anti-microbial agents.

A. In vitro Testing

In vitro methods of determining the ability of candidate compounds to inhibit, prevent or eradicate the growth of microbial cells are well-known in the art. In general, these methods involve contacting a culture of the cells of interest with various concentrations of the candidate compound and monitoring the growth of the cell culture relative to an untreated control culture. A second control culture comprising cells contacted with a known anti-microbial agent may also be included in such tests, if desired.

For example, the ability of a candidate compound of Formula I to inhibit the growth of microbial cells can readily be determined by measurement of the minimum inhibitory concentration (MIC) for the compound. The MIC is defined as the lowest concentration that inhibits growth of the organism to a pre-determined extent. For example, a $MIC_{100}$ value is defined as the lowest concentration that completely inhibits growth of the organism, whereas a $MIC_{90}$ value is defined as the lowest concentration that inhibits growth by 90% and a $MIC_{50}$ value is defined as the lowest concentration that inhibits growth by 50%. MIC values are sometimes expressed as ranges, for example, the $MIC_{100}$ for a compound may be expressed as the concentration at which no growth is observed or as a range between the concentration at which no growth is observed and the concentration of the dilution which immediately follows.

Typically, anti-bacterial MICs for candidate compounds are measured using a broth macro- or microdilution assay (see Amsterdam, D. (1996) "Susceptibility testing of antimicrobials in liquid media," pp. 52-111. In Loman, V., ed. *Antibiotics in Laboratory Medicine*, 4th ed. Williams and Wilkins, Baltimore, Md.). A standardised anti-bacterial susceptibility test is provided by the National Committee for Clinical Laboratory Standards (NCCLS) as NCCLS, 2000; document M7-A58.

In the classical broth microdilution method, the candidate anti-bacterial compound is diluted in culture medium in a sterile, covered 96-well microtiter plate. An overnight culture of a single bacterial colony is diluted in sterile medium such that, after inoculation, each well in the microtiter plate contains an appropriate number of colony forming units (CFU)/ml (typically, approximately $5 \times 10^5$ CFU/ml). Culture medium only (containing no bacteria) is also included as a negative control for each plate and known antibiotics are often included as positive controls. The inoculated microtiter plate is subsequently incubated at an appropriate temperature (for example, 35° C.-37° C. for 16-48 hours). The turbidity of each well is then determined by visual inspection and/or by measuring the absorbance, or optical density (OD), at 595 nm or 600 nm using a microplate reader and is used as an indication of the extent of bacterial growth.

Techniques for determining anti-fungal MIC values for candidate compounds are similar to those outlined above for anti-bacterial MICs and include both macrodilution and microdilution methods (see, for example, Pfaller, M. A., Rex, J. H., Rinaldi, M. G., *Clin. Infect. Dis.*, (1997) 24:776-84). A standardised anti-fungal susceptibility test method, NCCLS M27-T, has been proposed by the NCCLS (see, Ghannoum, M. A., Rex, J. H. and Galgiani J. N., *J. Clin. Microbiol.*, (1996) 34:489-495; Pfaller, M. A. and Yu, W. L., *Infect. Dis. Clin. North Amer.*, (2001) 15:1227-1261).

In accordance with one embodiment of the present invention, a compound of Formula I is considered to have an anti-microbial effect against a given micro-organism when used alone when the MIC of the compound for complete inhibition of growth of the organism is less than about 75 µg/ml. In one embodiment, the compound has a MIC less than about 50 µg/ml for the relevant micro-organism. In another embodiment, the compound has a MIC of less than about 35 µg/ml. In other embodiments, the compound has a MIC of less than about 25 µg/ml, less than about 16 µg/ml and less than about 12.5 µg/ml for the relevant micro-organism.

Anti-microbial effects may also be expressed as the percentage (%) inhibition of growth of a given micro-organism over a pre-determined period of time by treatment with a single concentration of a candidate compound. This method provides a rapid method of assessing the ability of a compound to inhibit microbial growth, for example, prior to conducting more in-depth tests, such as MIC determinations or in vivo testing. In one embodiment of the present invention, a candidate compound is considered to be a potential anti-microbial agent when it is capable of inhibiting the growth of a given micro-organism by about 25% when used at a concentration of about 25 µg/ml, with growth of the micro-organism being assessed over a 48 hour period.

One skilled in the art will appreciate that compounds that exhibit poor anti-microbial activity when used alone (for example, a compound that has a MIC of >128 µg/ml) may still be capable of good anti-microbial activity when used in combination with one or more known anti-microbial agents. For example, the compound may sensitise the microbial cells to the action of the other agent(s), it may act in synergy with agent(s), or it may otherwise potentiate the activity of the agent(s).

As such, many anti-microbial compounds show maximal effects when used in combination with a second drug. The effects can be simply additive, or they can be synergistic. For example, a compound that exhibits only bacteriostatic effects when used in isolation can become bacteriocidal when used in combination with a second anti-bacterial compound. Thus, the present invention contemplates that the anti-microbial activity of a compound of Formula I may be enhanced by the presence of another compound of Formula I, or by the presence of another known anti-microbial agent. Alternatively, the compound of Formula I may enhance the anti-microbial effect of other anti-microbial agents. Methods of testing for synergistic and/or additive effects between two or more compounds are well-known in the art.

For example, the fractional inhibitory concentration (FIC) can be used to assess the presence or absence of synergy between two anti-bacterial compounds (see, for example, U.S. Pat. No. 6,288,212). FICs are determined in microtiter plates in a similar manner to MICs, except that FICs are performed using a checkerboard titration of, for example, candidate compounds in one dimension and known antibiotics in the other dimension. The FIC is calculated by evaluating the impact of one antibiotic on the MIC of the other and vice versa. As used herein, FIC can be determined as follows:

$$FIC = \frac{MIC\text{(candidate compound in combination)}}{MIC\text{(candidate compound alone)}} + \frac{MIC\text{(known antibiotic in combination)}}{MIC\text{(known antibiotic alone)}}$$

An FIC value equal to one indicates that the influence of the compounds is additive and an FIC value of less than one indicates synergy. An FIC value of less than 0.5 is typically obtained for synergism.

B. In Vivo Testing

The ability of a compound of Formula I to act as an anti-microbial agent can also be tested in vivo using standard techniques. A number of animal models are known in the art that are suitable for testing the activity of anti-microbial compounds and are readily available.

Representative examples of animal models suitable for testing the anti-bacterial activity of a compound of Formula I in vivo include, but are not limited to, the immunosuppressed mouse as a model of acute *Staphylococcus aureus* infection, the burnt mouse or neutropenic mouse as a model for *Pseudomonas aeruginosa* infections and the suckling mouse for *Vibrio cholerae* infection of the intestine (Klose, et al., (2000), *Trends Microbiol.*, 8:189-91).

Other examples of suitable models and procedures for in vivo testing of anti-bacterial compounds are described in Iwahi, T., et al., *J. Med. Microbiol.*, (1982) 15:303-316; Michie, H. R., *J. Antimicrob. Chemother.*, (1998) 41:47-49; Yanke, S. J., et al., *Can. J. Microbiol.*, (2000) 46:920-926; Shibata, K., et al., *J. Antimicrob. Chemother.*, (2000) 45:379-82; Totsuka, K., et al., *J. Antimicrob. Chemother.*, (1999) 44:455-60; Goto, Y., et al., *Int. J. Antimicrob. Agents.*, (1999) 11:39-46.

Representative examples of animal models suitable for testing the anti-fungal activity of a compound of Formula I in vivo include, but are not limited to, the severe combined immunodeficiency (SCID) mouse model and a colostrum-deprived SPF piglet model for *Cryptosporidium parvum* infection, a granulocytopenic rabbit model of disseminated Candidiasis (see, for example, Walsh, et al., *J. Infect. Dis.*, 1990, 161:755-760; Thaler, et al., *J. Infect. Dis.*, 1988, 158:80), a mouse model of disseminated Aspergillosis (see, for example, Arroyo, et al., *Antimicrob. Agents Chemoth.*, 1977, pp. 21-25) and a neutropenic rat model of disseminated Candidiasis (see, for example, Lechner, et al., *Am. J. Physiol. (Lung Cell. Mol. Physiol.)* 1994, 10:1-8).

Methods for conducting in vivo tests to determine the activity of anti-microbial compounds are well-known in the art. Typically, in vivo testing comprises introducing a selected micro-organism into the appropriate animal model in a sufficient amount to cause infection, followed by administration of one or more doses of the test compound of Formula I. Methods of administration will vary depending on the compound being employed, but can be, for example, by way of bolus infusion into a suitable vein (such as the tail vein of mice or rats), or by oral administration. Animals treated with a known anti-microbial agent and/or with a saline or buffer control solution serve as controls. Repeat doses of the test compound may be administered to the animal, if necessary, at appropriate time intervals. The animals are subsequently monitored daily for mortality.

In accordance with the present invention, a compound of Formula I is considered to exert an in vivo anti-microbial effect if it results in a decrease in mortality of at least about 15% in a treated animal compared to a test animal. In one embodiment of the present invention, the compound of Formula I results in a decrease in mortality of at least about 25% in the treated animal. In another embodiment, the compound results in a decrease in mortality of at least about 40%. In other embodiments, the compound results in a decrease in mortality of at least about 50%, 60%, 70%, 80% and 90% in the treated animal.

IV. Toxicity Testing

It is important that the anti-microbial compounds of the present invention exhibit low toxicity in vivo. Toxicity tests for potential drugs are well-known in the art (see, for example, Hayes, A. W., ed., (1994), *Principles and Methods* of *Toxicology*, 3$^{rd}$ ed., Raven Press, NY; Maines, M., ed., *Current Protocols in Toxicology*, John Wiley & Sons, Inc., NY).

In vitro acute toxicity testing of a compound of Formula I can be performed using mammalian cell lines (see, for example, Ekwall, B., *Ann. N.Y. Acad. Sci.*, (1983) 407:64-77). Selection of an appropriate cell line is dependent on the potential application of the candidate compound and can be readily determined by one skilled in the art.

In vivo toxicity testing can be performed by standard methodology. For example, by injecting varying concentrations of the candidate compound into an appropriate animal model. The compound can be injected once, or administration can be repeated over several days. The toxic effects of the compound can be evaluated over an appropriate time period by monitoring the general health and body weight of the animals. After the completion of the period of assessment, the animals can be sacrificed and the appearance and weight of the relevant organs determined.

In accordance with one embodiment of the present invention, a compound of Formula I for use in vivo shows both good anti-microbial activity and low or no toxicity at the concentration at which it would be administered as an anti-microbial agent.

V. Uses of the Anti-Microbial Compounds of Formula I

The present invention provides for the use of one or more compounds of Formula I for the inhibition, prevention or eradication of the growth and/or proliferation of bacteria and/or fungi, either alone or in combination with one or more other compounds of Formula I or known anti-microbial agents.

Thus, in one embodiment, the present invention provides a method of inhibiting bacterial growth by contacting a bacterium with an effective amount of one or more compounds of Formula I. The compounds of Formula I may have broad spectrum anti-bacterial activity, in which case they may be used against gram-positive or gram-negative bacteria. Representative examples of bacteria that may be inhibited by compounds of Formula I include, but are not limited to, *Corynebacterium xerosis, Chlamydia pneumoniae, Chlamydia trachomatis, Enterobacter cloacae, Enterobacter faecalis, Enterococcus faecium, Escherichia coli, Escherichia coli* O157:H7, *Haemophilus influenzae, Helicobacter pylori, Listeria monocytogenes, Moraxella catarrhalis, Neisseria gonorrhoae, Neisseria meningitidis, Pseudomonas aeruginosa, Pneumococci* species, *Salmonella enterica, Salmonella typhimurium, Staphylococcus aureus, Staphylococcus aureus* K147, *Staphylococcus epidermidis, Staphylococcus typhimurium, Streptococcus mitis, Streptococcus pneumoniae, Streptococcus pyogenes, Vibrio cholerae, Mycobacterium tuberculosis* and other acid-fast staining bacteria (i.e. *M. africanum, M. avium-intracellulare, M. pneumoniae, M. bovis, M. leprae, M. phlei*), *Bacillus anthracis* and other endospore-forming rods and cocci. In one embodiment of the present invention, the compounds are used against gram-positive bacteria.

It is well-established in the field of microbiology that many multidrug-resistant strains of bacteria have emerged in the recent past and will continue to emerge with the continued use of standard antibiotics. Examples of currently known resistant strains of bacteria include methicillin-resistant *Staphylococcus aureus* (MRSA), methicillin-resistant coagulase-negative staphylococci (MRCNS), penicillin-resistant *Streptococcus pneumoniae*, penicillin-resistant pneumococci and multidrug-resistant *Enterococcus faecium*. The present invention, therefore, contemplates the use of compounds of Formula I in the inhibition of growth of such multidrug-resistant strains. In one embodiment of the present invention, compounds of Formula I are used to inhibit the growth of multidrug-resistant strains of bacteria. In another embodiment, the compounds are used to inhibit the growth of MRSA.

In accordance with one embodiment of the present invention, one or more compounds of Formula I can be administered in a therapeutically effective amount alone or in combination with one or more other anti-bacterial agents to a subject with a bacterial disorder. Thus, the present invention provides the use of one or more of the compounds of Formula I in the treatment of bacterial infections and bacterially-related disorders and diseases. Examples of bacterially-related disorders and diseases that may be treated with the compounds of the present invention include, but are not limited to, tuberculosis, meningitis, ulcers, septicaemia, bacteremia, cystic fibrosis, pneumonia, typhoid fever, bacterial conjunctivitis, gonorrhoea, impetigo, bacterial eye or ear infections, bacterial diarrhoea, cystitis, bacterial vaginitis, bacterial endocarditis, bacterial pericarditis, peliosis, superficial skin infections, toxic shock, food poisoning, hemolytic uremic syndrome, botulism, leprosy, gangrene, tetanus, lyme disease, plague, anthrax and chancroid.

In another embodiment, the present invention provides a method of inhibiting fungal growth by contacting a fungus with an effective amount of one or more compounds of Formula I either alone or in combination with one or more other anti-fungal agents. Representative examples of fungi that may be inhibited with compounds of Formula I include, but are not limited to, *Histoplasma* (e.g. *H. capsulstum*), *Coccidioides, Blastomyces, Paracoccidioides, Cryptococcus* (e.g. *C. neoformans*), *Aspergillus* (e.g. *A. fumigatus, A. flaws, A. niger, A. nidulans, A. terreus, A. sydowi, A. flavatus*, and *A. glaucus*), *Zygomycetes* (e.g. *Basidiobolus, Conidiobolus, Rhizopus, Mucor, Absidia, Mortierella, Cunninghamella*, and *Saksenaea*), *Candida* (e.g. *C. albicans, C. tropicalis, C. parapsilosis, C. stellatoidea, C. krusei, C. parakrusei, C. lusitaniae, C. pseudorropicalis, C. guilliermondi* and *C. glabrata*), *Cryptosporidium parvum, Sporothrix schenckii, Piedraia hortae, Trichosporon beigelii, Malassezia furfur, Phialophora verrucosa, Fonsecae pedrosoi, Madurella mycetomatis* and *Pneumocystis carinii*.

In accordance with another embodiment of the present invention, one or more anti-microbial compounds of Formula I can be administered in a therapeutically effective amount either alone or in combination with other anti-fungal agents to a subject with a fungal infection or fungally-related disorder or disease. Examples of fungally-related disorders and diseases that may be treated with the compounds of Formula I include, but are not limited to, Candidiasis; endemic mycoses (such as Histoplasmosis, Coccidioidomycosis, Blastomycosis, Paracoccidioidomycosis, Cryptococcosis, Aspergillosis, Mucormycosis), associated disseminated infections and progressive pulmonary disease; cryptococcal meningitis; narcotising patchy bronchopneumonia; haemorrhagic pulmonary infarction; rhinocerebral disease; neutropenia, black piedra; white piedra; tinea (versicolor, capitis, corporis, etc.); *Pneumocystis* pneumonia; chromoblastomycosis, and maduromycosis.

In accordance with a further embodiment of the present invention, one or more compounds of Formula I may be used as therapeutic agents in combination with one or more known drugs in combination or synergistic therapy for the treatment of microbial infection, or disorders or diseases associated therewith. Such therapy is known in the art and selection of the appropriate drug(s) to be administered with compound(s) of Formula I is readily discernible by one of skill in the art. For example, in the treatment of bacterial infections and related diseases, useful classes of antibiotics for combination or synergistic therapy include, but are not limited to, aminoglycosides, penicillins, cephalosporins, fluoroquinolones, quinolones, carbapenems, tetracyclines, glycopeptides and macrolides, and other antibiotics such as chloramphenicol, clindamycin, trimethoprim, sulphamethoxazole, nitrofurantoin, rifampin and mupirocin. For the treatment of fungal infections and fungally-related diseases, candidate antimicrobial compounds for combination therapy include, but are not limited to, amphotericin B and the structurally related compounds nystatin and pimaricin; flucytosine; azole derivatives such as ketoconazole, clotrimazole, miconazole, econazole, butoconazole, oxiconazole, sulconazole, terconazole, fluconazole and itraconazole; allylamines-thiocarbamates, such as tolnaftate and naftifme, and griseofulvin.

The present invention also contemplates the use of compounds of Formula I as the active ingredient in anti-microbial cleansers, polishes, paints, sprays, soaps, or detergents. The compounds can also be included as an anti-microbial agent in cosmetic, personal care, household and industrial products, for example, to improve shelf-life by inhibiting the growth of microbes within the products. The compounds may be formulated for application to surfaces to inhibit the growth of a microbial species thereon, for example, surfaces such as countertops, desks, chairs, laboratory benches, tables, floors, sinks, showers, toilets, bathtubs, bed stands, tools or equipment, doorknobs and windows. Alternatively, the compounds may be formulated for laundry applications, for example, for washing clothes, towels, sheets and other bedlinen, washcloths or other cleaning articles. The antimicrobial cleansers, polishes, paints, sprays, soaps, or detergents according to the present invention can optionally contain suitable solvent(s), carrier(s), thickeners, pigments, fragrances, deodorisers, emulsifiers, surfactants, wetting agents, waxes, or oils. In one embodiment, the present invention provides a formulation containing one or more compounds of Formula I for external use as a pharmaceutically acceptable skin cleanser. The cleansers, polishes, paints, sprays, soaps, and detergents according to the present invention are useful institutions, such as in hospital settings for the prevention of nosocomial infections, as well as in home settings.

In addition, the invention contemplates the use of compounds of Formula I in formulations to kill or inhibit the growth of microbial species in food preparations, or to sterilise surgical and other medical equipment and implantable devices, including prosthetic joints. The compounds can also be formulated for use in the in situ sterilisation of indwelling invasive devices such as intravenous lines and catheters, which are often foci of infection.

The present invention further contemplates the use of the compounds of Formula I as the active ingredient in personal care items, such as soaps, deodorants, shampoos, mouthwashes, toothpastes, and the like. Many compositions used in personal care applications are susceptible to microbial growth and it is thus desirable to incorporate into these compositions an effective anti-microbial material. The anti-microbial agent may be incorporated into the personal care formulation using techniques known in the art. Thus, the anti-microbial agent may be added to the personal care formulation as a solution, emulsion or dispersion in a suitable liquid medium. Alternatively, the anti-microbial agent may be added, undiluted, to the personal care formulation or may be added with a solid carrier or diluent. The anti-microbial agent may be added to the pre-formed personal care formulation or may be added during the formation of the personal care formulation, either separately or premixed with one of the other components of the formulation.

VI. Pharmaceutical Formulations and Administration of Anti-Microbial Compounds of Formula I For use as therapeutic agents in the treatment of microbial infections, or disorders or diseases associated therewith in a subject, the anti-microbial compounds of the present invention are typically formulated prior to administration. Therefore, the present invention provides pharmaceutical formulations comprising one or more compounds of Formula I and a pharmaceutically-acceptable carrier, diluent, or excipient. The present pharmaceutical formulations are prepared by standard procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material that acts as a vehicle, excipient, or medium for the active ingredient.

The pharmaceutical compositions comprising the anti-microbial compounds according to the present invention may be administered in a number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g. intrathecal or intraventricular, administration.

The anti-microbial compounds of the present invention may be delivered alone or in combination, and may be delivered along with a pharmaceutically acceptable vehicle. Ideally, such a vehicle would enhance the stability and/or delivery properties. The present invention also provides for administration of pharmaceutical compositions comprising one or more of the compounds of Formula I using a suitable vehicle, such as an artificial membrane vesicle (including a liposome, niosome and the like), microparticle or microcapsule. The use of such vehicles may be beneficial in achieving sustained release of the anti-microbial compound(s).

For administration to an individual for the treatment of an infection or disease, the present invention also contemplates the formulation of the pharmaceutical compositions comprising the anti-microbial compounds into oral dosage forms such as tablets, capsules and the like. For this purpose, the compounds can be combined with conventional carriers, such as magnesium carbonate, magnesium stearate, talc, sugar, lactose, pectin, dextrin, starch, gelatine, tragacanth, methylcellulose, sodium carboxymethyl-cellulose, low melting wax, cocoa butter and the like. Diluents, flavouring agents, solubilizers, lubricants, suspending agents, binders, tablet-disintegrating agents and the like can also be employed, if required. The anti-microbial compounds can be encapsulated with or without other carriers. In accordance with the present invention, the proportion of anti-microbial compound(s) in any solid and liquid composition will be at least sufficient to impart the desired activity to the individual being treated upon oral administration. The present invention further contemplates parenteral injection of the anti-microbial compounds, in which case the compounds are formulated as a sterile solution containing other solutes, for example, enough saline or glucose to make the solution isotonic.

For administration by inhalation or insufflation, the anti-microbial compounds can be formulated into an aqueous or partially aqueous solution, which can then be utilized in the form of an aerosol. Aqueous formulations of the anti-microbial compounds of the present invention may also be used in the form of ear or eye drops, or ophthalmic solutions. The present invention further contemplates topical use of the anti-microbial compounds. For this purpose they can be formulated as dusting powders, creams or lotions in pharmaceutically acceptable vehicles, which are applied to affected portions of the skin.

Compositions intended for oral use may be prepared according to procedures known in the art for the manufacture of pharmaceutical compositions and such compositions may further contain one or more sweetening agents, flavouring agents, colouring agents, preserving agents, or a combination thereof, in order to provide pharmaceutically elegant and palatable preparations. Tablets typically contain the anti-microbial compound(s) in admixture with non-toxic pharmaceutically acceptable excipients suitable for the manufacture of tablets, such as inert diluents, for example, calcium carbonate, sodium carbonate, lactose, calcium phosphate or sodium phosphate; granulating and disintegrating agents, for example, corn starch, or alginic acid; binding agents, for example, starch, gelatine or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the anti-microbial compound(s) is mixed with an inert solid diluent, for example, calcium carbonate, calcium phosphate or kaolin, or as soft gelatine capsules wherein the active ingredient is mixed with water or an oil medium, for example, peanut oil, liquid paraffin or olive oil.

Aqueous suspensions typically contain the anti-microbial compound(s) in admixture with excipients suitable for the manufacture of aqueous suspensions, such as suspending agents (for example, sodium carboxylmethylcellulose, methyl cellulose, hydropropylmethyl cellulose, sodium alginate, polyvinylpyrrolidone, gum tragacanth and gum acacia); dispersing or wetting agents such as a naturally-occurring phosphatide (for example, lecithin), or condensation products of an alkylene oxide with fatty acids (for example, polyoxyethylene stearate), or condensation products of ethylene oxide with long chain aliphatic alcohols (for example, heptadecaethyleneoxycetanol), or condensation products of ethylene oxide with partial esters derived from fatty acids and a hexitol (for example, polyoxyethylene sorbitol monooleate), or condensation products of ethylene oxide with partial esters derived from fatty acids and hexitol anhydrides (for example, polyethylene sorbitan monooleate). The aqueous suspensions may further contain one or more preservatives, for example, ethyl, or n-propyl-p-hydroxy benzoate; one or more colouring agents; one or more flavouring agents, or one or more sweetening agents, such as sucrose or saccharin, or a combination thereof.

Oily suspensions may be formulated by suspending the anti-microbial compound(s) in a vegetable oil, for example, peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the anti-microbial compound in admixture with a dispersing or wetting agent, suspending agent and one or more preservatives. Suitable dispersing or wetting agents and suspending agents are exemplified by those mentioned above. Additional excipients, for example, sweetening, flavouring and colouring agents, may also be present.

Pharmaceutical compositions of the present invention may also be in the form of oil-in-water emulsions. The oil phase may be a vegetable oil, for example, olive oil or peanut oil, or a mineral oil, for example, liquid paraffin, or mixtures thereof. Suitable emulsifying agents may be naturally-occurring gums (for example, gum acacia or gum tragacanth); naturally-occurring phosphatides (for example, soy bean lecithin), and esters or partial esters derived from fatty acids and hexitol anhydrides (for example, sorbitan monooleate), and condensation products of the partial esters with ethylene oxide (for example, polyoxyethylene sorbitan monooleate). The emulsions may also contain sweetening and flavouring agents.

Syrups and elixirs may be formulated with sweetening agents, for example, glycerol, propylene glycol, sorbitol or sucrose. Such formulations may also contain one or more demulcents, preservatives or flavouring and colouring agents, or combinations thereof.

The pharmaceutical compositions may be in the form of a sterile injectable aqueous or oleaginous suspension. This suspension may be formulated according to known art using suitable dispersing or wetting agents and suspending agents as described above. The sterile injectable preparation may also be a solution or a suspension in a non-toxic, parentally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Typically, a bland fixed oil is employed for this purpose such as a synthetic mono- or diglyceride. In addition, fatty acids such as oleic acid find use in the preparation of injectables. Adjuvants, such as local anesthetics, preservatives and buffering agents, may also be included in the injectable formulation.

The compound(s) of Formula I may be administered, together or separately, in the form of suppositories for rectal or vaginal administration of the compound. These compositions can be prepared by mixing the compound with a suitable non-irritating excipient which is solid at ordinary temperatures but liquid at the rectal/vaginal temperature and will therefore melt to release the compound. Examples of such materials include cocoa butter and polyethylene glycols.

Another formulation of the present invention employs transdermal delivery devices ("patches"). Such transdermal patches may be used to provide continuous or discontinuous infusion of the anti-microbial compounds of the present invention in controlled amounts. The construction and use of transdermal patches for the delivery of pharmaceutical agents is well known in the art (see, for example, U.S. Pat. No. 5,023,252; issued Jun. 11, 1991). Such patches may be constructed for continuous, pulsatile, or on demand delivery of pharmaceutical agents.

It may be desirable or necessary to introduce the pharmaceutical composition to the brain, either directly or indirectly. Direct techniques usually involve placement of a drug delivery catheter into the host's ventricular system to bypass the blood-brain barrier. An example of such an implantable delivery system, used for the transport of biological factors to specific anatomical regions of the body, is described in U.S. Pat. No. 5,011,472.

The dosage of the anti-microbial compound to be administered is not subject to defined limits, but will usually be an effective amount. In general, the dosage will be the equivalent, on a molar basis, of the pharmacologically active free form produced from a dosage formulation upon the metabolic release of the active free drug to achieve its desired pharmacological and physiological effects. The pharmaceutical compositions are typically formulated in a unit dosage form, each dosage containing from, for example, about 0.05 to about 100 mg of the anti-microbial compound. The term "unit dosage form" refers to physically discrete units suitable as unitary dosages for administration to human subjects and other animals, each unit containing a predetermined quantity of anti-microbial compound calculated to produce the desired therapeutic effect, in association with a suitable pharmaceutical excipient.

Typical daily dosages of the anti-microbial compounds fall within the range of about 0.01 to about 200 mg/kg of body weight in single or divided dose. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, for example, by first dividing larger doses into several smaller doses for administration throughout the day.

VII. Kits

The present invention additionally provides for therapeutic kits containing one or more compounds of Formula I in pharmaceutical compositions, alone or in combination with one or more other anti-microbial agents, for use in the treatment of infections and disease. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human or animal administration.

When the components of the kit are provided in one or more liquid solutions, the liquid solution can be an aqueous solution, for example a sterile aqueous solution. For in vivo use, the anti-microbial compound may be formulated into a pharmaceutically acceptable syringeable formulation. In this case the container means may itself be an inhalant, syringe, pipette, eye dropper, or other such like apparatus, from which the formulation may be applied to an infected area of the animal, such as the lungs, injected into an animal, or even applied to and mixed with the other components of the kit.

The components of the kit may also be provided in dried or lyophilised forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate composition within the body of an animal. Such an instrument may be an inhalant, syringe, pipette, forceps, measured spoon, eye dropper or any such medically approved delivery vehicle.

To gain a better understanding of the invention described herein, the following examples are set forth. It should be understood that these examples are for illustrative purposes only. Therefore they should not limit the scope of the invention in any way.

EXAMPLES

Preparation of Compounds

All reactions have been carried out according to the scheme shown below;

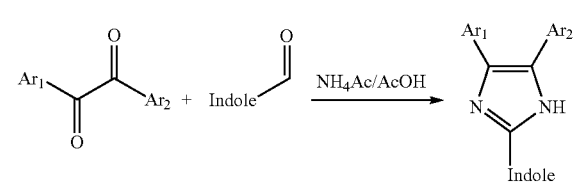

In a typical experimental procedure 1 mmol (1 equiv.) of the indole carboxyaldehyde was combined with 1.05-1.10 mmole (1.05-1.1 equiv.) of the benzil and 20 mmole (20 equiv.) of ammonium acetate and 5 ml of acetic acid. The mixture was magnetically stirred and heated to reflux for 3-5 hr. The reaction process was monitored by TLC, until complete consumption of the indole was achieved. The reaction mixture was cooled to room temperature and added dropwise into well-stirred ice-water. The suspension solid was then filtered and the crude solid was dissolved in ethyl acetate, dried over sodium sulfate and filtered, the organic solvent was removed by vacuum. The products was then either recrystallized with alcohol or separated by column chromatography using petroleum ether-Ethyl acetate as an eluant.

It is noteworthy that, the TLC of the products shows a characteristic blue florescent color under the UV (wave length $\lambda$=254 nm), a property used as an additional characterization feature. Melting points were recorded using a MEL-TEMP capillary melting point apparatus, the melting point are uncorrected. $^1$H-NMR was performed in a 500 MHz Brucker instrument at room temperature using a suitable deuterated solvent.

Example 1

Preparation of compound 2

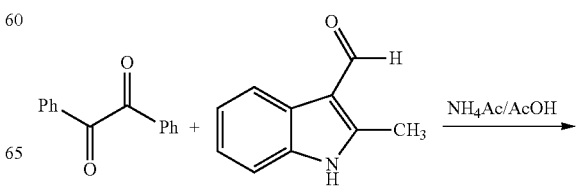

-continued

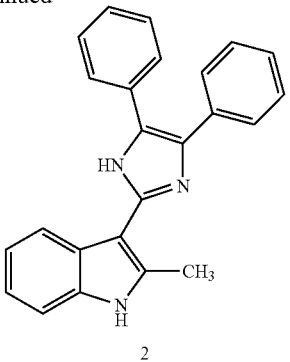

2

$^1$H-NMR: δ (DMSO-d$_6$), 12.10 (s, 1H), 11.30 (s, 1H), 7.98 (d, 1H), 7.62 (d, 2H), 7.56 (d, 2H), 7.45 (t, 2H), 7.28-7.40 (m, 4H), 7.24 (t, 1H), 7.03-7.14 (m, 2H), 2.70 (s, 3H). HRMS m/z for C$_{24}$H$_{19}$N$_3$ calc. Is 349.157898, found 349.157897. M.p.=decomposed at 260-264.

Example 2

Compound 5

$^1$H-NMR (CDCl$_3$): δ=8.02 (d, 2H), 7.53 (d, 1H), 7.43-7.52 (m, 6H), 7.41 (d, 1H), 7.21-7.34 (m, 6H), 2.81 (s, 3H), 2.75 (s, 3H). EIMS [M$^+$] m/z for C$_{28}$H$_{23}$N$_3$O$_2$ is 433. M.p.=224-227.

Example 3

Compound 11

$^1$H-NMR (CDCl$_3$): δ=7.70 (d, 1H), 7.41 (d, 4H), 7.32 (d, 1H), 7.09 (q, 2H), 6.77 (d, 4H), 2.95 (s, 12H), 2.67 (s, 3H). EIMS [M$^+$] m/z for C$_{28}$H$_{29}$N$_5$ is 435, M.p.=decomposed at 236-238.

Example 4

Compound 13

$^1$H-NMR (CDCl$_3$): δ=7.47 (d, 4H), 7.44 (d, 4H), 7.30-7.34 (m, 1H), 7.14-7.19 (m, 3H), 2.68 (bs, 3H), EIMS [M$^+$] m/z for C$_{24}$H$_{17}$N$_3$Br$_2$ is 507. M.p.=240-245.

Example 5

Compound 19

$^1$H-NMR (DMSO-d$_6$): δ=12.13 (s, 1H), 11.33 (s, 1H), 7.94 (d, 2H), 7.57 (d, 2H), 7.52 (bd, 2H), 7.39 (bd, 2H), 7.35 (d, 1H), 7.05-7.12 (m, 3H), 2.50 (s, 3H). EIMS [M$^+$] m/z for C$_{24}$H$_{17}$N$_3$Cl$_2$ is 418. M.p.=165-167.

Example 6

Compound 29

$^1$H-NMR (DMSO-d$_6$): δ=8.83 (q, 2H), 8.73 (m, 1H), 8.68 (d, 1H), 8.46 (d, 1H), 8.24 (s, 1H), 7.74 (t, 2H), 7.62 (t, 2H), 7.51-7.56 (m, 1H), 7.23-7.27 (m, 2H), 2.71 (s, 3H). EIMS [M$^+$] m/z for C$_{23}$H$_{15}$N$_3$ is 303. M.p.=135-137.

Example 7

Compound 31

$^1$H-NMR (CDCl$_3$): δ=8.90 (bs, 1H), 7.62 (bs, 1H), 7.48 (bd, 4H), 7.34 (m, 4H), 7.21 (m, 1H), 7.13 (m, 2H), 2.43 (bs, 3H). EIMS [M$^+$] m/z for C$_{23}$H$_{15}$N$_3$ClBr is 448. M.p.=decomposed at 218-220.

Example 8

Compound 35

$^1$H-NMR (CDCl$_3$): δ=7.78 (bs, 1H), 7.59 (d, 2H), 7.54 (d, 2H), 7.35-7.39 (m, 2H), 7.28-7.34 (m, 2H), 7.13-7.18 (m, 2H), 7.01-7.05 (m, 2H), 2.72 (bs, 3H). EIMS [M$^+$] m/z for C$_{24}$H$_{18}$N$_3$F is 367. M.p.=decomposed at 247-250.

Example 9

Compound 38

$^1$H-NMR (Acetone-d$_6$): δ=11.12 (bs, 1H), 10.46 (bs, 1H), 8.12 (d, 1H), 7.80 (bd, 2H), 7.62 (bd, 2H), 7.38-7.48 (m, 5H), 6.98-7.22 (m, 12H), 2.84 (bs, 3H). EIMS [M$^+$] m/z for C$_{36}$H$_{27}$N$_3$O$_2$ is 533. M.p.=decomposed at 128-130.

Example 10

Compound 40

$^1$H-NMR (CDCl$_3$): δ=8.12 (dd, 2H), 7.60 (m, 6H), 7.24-7.53 (m, 10H), 6.87 (bd, 2H), 6.61 (bd, 2H), 2.08 (s, 3H). M.p.=decomposed at 142.

Example 11

Compound 42

$^1$H-NMR (CDCl$_3$): δ=9.39 (bs, 1H), 7.39-7.50 (m, 4H), 7.28-7.38 (m, 6H), 7.06 (bs, 1H), 6.94 (bs, 2H), 2.08 (bs, 3H). EIMS [M$^+$] m/z for C$_{24}$H$_{18}$N$_3$Br is 428. M.p.=decomposed at 155-157.

Example 12

Compound 44

$^1$H-NMR (CDCl$_3$): δ=8.78 (dd, 2H), 8.19 (dd, 1H), 7.96 (bs, 1H), 7.80 (dd, 1H), 7.80 (dd, 1H), 7.55-7.77 (m, 6H), 7.16-7.42 (m, 2H), 2.87 (bs, 3H). EIMS [M$^+$] m/z for C$_{24}$H$_{17}$N$_3$ is 347. M.p.=decomposed at 167.

Example 13

Compound 10

$^1$H-NMR (CDCl$_3$): δ=10.68 (bs, 1H), 7.73 (bs, 1H), 7.22 (d, 4H), 6.99 (bs, 1H), 6.92 (bd, 2H), 6.85 (bd, 2H), 6.611 (d, 4H), 3.70 (s, 6H). EIMS [M$^+$] m/z for C$_{25}$H$_{20}$N$_3$BrO$_2$ is 474. M.p.=135.

Example 14

Compound 26

$^1$H-NMR (DMSO-d$_6$): δ=12.60 (s, 1H), 11.70 (s, 1H), 8.60 (d, 1H), 8.17 (s, 1H), 7.68 (bs, 1H), 7.46 (d, 2H), 7.33 (d, 2H), 7.25 (bs, 2H), 7.09 (bs, 1H). EIMS [M$^+$] m/z for C$_{19}$H$_{12}$N$_3$BrS$_2$ is 426.

Example 15

Compound 28

$^1$H-NMR (DMSO-d$_6$): δ=12.60 (s, 1H), 11.65 (s, 1H), 8.44-8.64 (m, 3H), 8.01-8.14 (m, 1H), 7.22-7.66 (m, 8H). EIMS [M$^+$] m/z for C$_{22}$H$_{14}$N$_4$BrF is 433. M.p.=decomposed at 343.

Example 16

Compound 32

$^1$H-NMR (CDCl$_3$): δ=8.12 (bs, 1H), 7.48 (d, 2H), 7.46 (d, 2H), 7.23-7.34 (m, 8H).
M.p.=230-232.

Example 17

Compound 34

$^1$H-NMR (DMSO-d$_6$): δ=12.63 (s, 1H), 11.67 (s, 1H), 8.62 (d, 1H), 8.21 (d, 2H), 8.08 (d, 1H), 7.86 (d, 2H), 7.39-7.64 (m, 6H), 7.32 (dd, 1H). EIMS [M$^+$] m/z for C$_{23}$H$_{15}$N$_4$BrFO$_2$ is 459. M.p.=decomposed at 250-253.

Example 18

Compound 36

$^1$H-NMR (CDCl$_3$): δ=10.42 (bs, 1H), 7.86 (s, 1H), 7.16-7.33 (m, 6H), 7.04 (dd, 2H), 6.95 (dd, 2H), 6.88 (t, 3H). EIMS [M$^+$] m/z for C$_{23}$H$_{15}$N$_3$BrF is 432. M.p.=decomposed at 83-86.

Example 19

Compound 41

$^1$H-NMR (CDCl$_3$): δ=8.08 (d, 4H), 8.07 (bs, 1H), 7.75 (d, 4H), 7.28-7.50 (m, 10H), 7.12 (bd, 2H), 6.97 (bs, 1H). M.p.=155-158.

Example 20

Compound 43

$^1$H-NMR (CDCl$_3$): δ=9.75 (bs, 1H), 7.83 (bs, 1H), 7.36 (m, 3H), 7.25-7.29 (m, 5H), 7.12 (m, 3H), 7.10 (bd, 1H). EIMS [M$^+$] m/z for C$_{23}$H$_{15}$N$_3$Br$_2$ is 493. M.p.=decomposed at 230.

Example 21

Compound 45

$^1$H-NMR (DMSO-d$_6$): δ=13.30 (bs, 1H), 11.62 (d, 1H), 8.87 (bd, 2H), 8.64 (bs, 1H), 8.44 (bs, 1H), 8.29 (t, 1H), 7.76 (t, 2H), 7.62 (t, 2H), 7.52 (d, 1H), 7.35-7.41 (m, 2H). EIMS [M$^+$] m/z for C$_{23}$H$_{14}$N$_3$Br is 412.

Example 22

Compound 84

$^1$H-NMR (DMSO-d$_6$): δ=8.64 (d, 1H), 8.17 (d, 1H), 7.47 (d, 1H), 7.39 (t, 1H), 7.33 (dd, 1H), 7.20-7.31 (m, 2H), 7.12 (bd, 2H), 6.97 (bd, 1H), 6.84 (bd, 1H), 3.77 (s, 3H), 3.72 (s, 3H), EIMS [M$^+$] m/z for C$_{25}$H$_{20}$N$_3$BrO$_2$ is 474. M.p.=decomposed at 250-253.

Example 23

Compound 37

$^1$H-NMR (CDCl$_3$): δ=9.92 (bs, 1H), 8.17 (bs, 1H), 7.87 (t, 1H), 7.55 (bs, 1H), 7.21-7.33 (m, 6H), 7.15-7.2 (m, 1H), 7.04-7.07 (m, 2H), 6.90 (t, 2H).). EIMS [M$^+$] m/z for C$_{23}$H$_{16}$N$_3$F is 353. M.p.=51.

Example 24

Compound 46

$^1$H-NMR (DMSO-d$_6$): δ=13.09 (s, 1H), 11.61 (d, 1H), 8.83 (q, 2H), 8.73 (m, 1H), 8.68 (d, 1H), 8.46 (d, 1H), 8.24 (s, 1H), 7.74 (t, 2H), 7.62 (t, 2H), 7.51-7.56 (m, 1H), 7.23-7.27 (m, 2H). EIMS [M$^+$] m/z for C$_{23}$H$_{15}$N$_3$ is 333. M.p.=135-137.

Example 25

Compound 83

$^1$H-NMR (DMSO-d$_6$): δ=12.40 (s, 1H), 11.80 (s, 1H), 8.56 (d, 1H), 8.24 (s, 1H), 8.15 (s, 1H), 7.78 (d, 1H), 7.65 (d, 2H), 7.54 (d, 2H), 7.47 (t, 2H), 7.32-7.42 (m, 3H), 7.24 (t, 1H), 3.90 (s, 3H). EIMS [M$^+$] m/z for C$_{25}$H$_{19}$N$_3$O$_2$ is 393. M.p.=293-295.

Example 26

Compound 74

$^1$H-NMR (DMSO-d$_6$): δ=11.74 (d, 1H), 7.95 (dd, 1H), 7.32-7.57 (m, 6H), 7.17-7.31 (m, 2H), 7.12 (t, 1H), 6.70 (d, 1H), 6.66 (bd, 1H). EIMS [M$^+$] m/z for C$_{23}$H$_{19}$N$_2$FO$_2$ is 374.

Example 27

In Vitro Inhibition of Methicillin-Resistant *Staphylococcus aureus* (MRSA)

CMRSA-1B is an epidemic multi-drug resistant strain of *S. aureus* which accounts for 49% and 70% of *S. aureus* strains isolated in hospitals in Canada and in Ontario respectively. CMRSA-1B was cultured in Tryptic Soy Broth (TSB) at 37° C. and used for the inhibition assays during the log phase of growth (OD$_{600}$ of 0.1). 10 µl of each candidate compound were placed in duplicate into the wells of a 96-microtitre plate followed by the addition of 90 µl of the CMRSA-1B culture suspensions. The candidate compounds were dissolved at a concentration of 250 µg/ml in 50% DMSO, and diluted to a final concentration of 25 µg/ml in 5% DMSO in the culture suspension. Bacterial growth was monitored by measuring the absorbance at 600 nm in an ELISA reader. The level of growth inhibition was estimated as percentage of the OD$_{600}$ value with respect to a control consisting of an aliquot of the same bacterial suspension in the presence of 5% DMSO.

A. Determination of Minimal Inhibitory Concentration (MIC)

The lowest concentration of triaryl-imidazole derivative that completely inhibited growth of the micro-organisms in vitro (MIC) was determined by the sequential macrodilution (tube) broth method. (Nat. Committee for Clinical Laboratory Standards. Document M7-A5 2000, 20; 1-25). Bacterial suspensions containing 5×10$^5$ colony-forming units (CFU) were incubated with serial two-fold dilutions of each drug at 37° C. overnight, and growth was monitored visually. The range of MIC values among the triaryl-imidazole derivatives was 12.5-50 µg/ml. Table 1 shows the MIC value for some of the 2,4,5-triarylimidazole-derivatives against MRSA.

TABLE 1

| Conc. µg/ml | Compound 1 | Compound 2 | Compound 3 | Compound 4 |
|---|---|---|---|---|
| 0 | + | + | + | + |
| 3.12 | + | + | + | + |
| 6.25 | + | + | + | + |
| 12.50 | – | – | + | + |
| 25.00 | – | – | – | + |
| 50.00 | – | – | – | – |
| 100.00 | – | – | – | – |

(+): Positive visual bacterial growth
(–): Negative visual bacterial growth

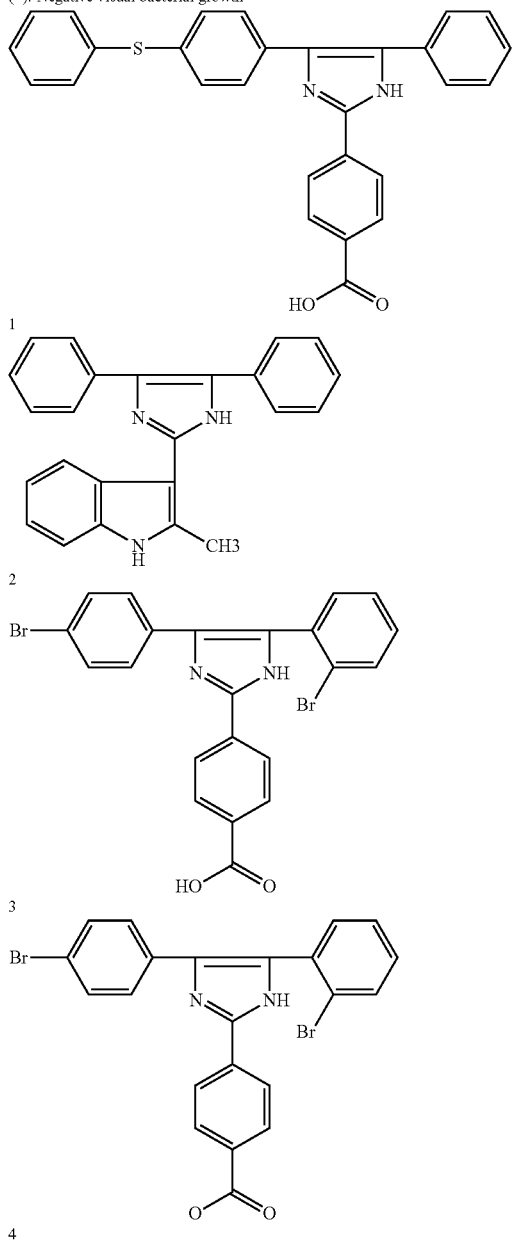

B. Bactericidal Effect against MRSA

The bactericidal effect of compounds of Formula I against MRSA was determined using the same concentrations of compounds and growth conditions used to determine the MICs (see above). Serial dilutions of liquid cultures were incubated with the compounds at 37° C. overnight and then plated on Tryptic Soy Agar (TSA) plates. After incubation for 17 hours at 37° C., the number of live bacteria was calculated from the number of colonies grown per milliliter of culture and expressed as colony-forming units (CFU). A bactericidal effect was observed at the corresponding MIC for derivatives 1 and 2, while derivatives 3 and 4 exhibited a bacteriostatic effect at these concentrations (FIG. 1).

Example 28

In Vivo Inhibition of Methicillin-Resistant *Staphylococcus aureus* (MRSA)

Triaryl-imidazole compounds were tested in vivo for antibacterial activity against MRSA in a model of acute infection using immunosuppressed mice. Suspensions of 400 µL containing $5 \times 10^6$ MRSA-1B387 bacteria in 5% mucin were injected into groups of 5-10 female, 8-14 weeks CB17-SCID mice. Under these conditions bacterial infection produced 80-100% lethality in less than 48 hours. Each group of inoculated mice was treated with 50 mg/kg of the respective compound intraperitoneally (I.P.) immediately and 3 hours after bacterial inoculation. The results of the in vivo experiments are shown in Table 2.

TABLE 2

| Compound | No. of Experiments | Survival (%) |
|---|---|---|
| 1 | 1 | 40 |
| 2 | 1 | 80 |
| 3 | 2 | 15 |
| 4 | 3 | 50 |
| Vancomycin | 2 | 100 |
| Control | 4 | 24 |

Example 29

In Vivo Toxicity Tests

In vivo acute toxicity tests were conducted using compounds 1, 2, 3 and 4. Mice were injected with each of the above compounds at a concentration of 200 mg/kg per day. No symptoms of sickness, change of total weight, organ weight and appearance was observed in any of the mice challenged, indicating that these compounds exhibit no toxic effects in mice.

Further in vivo GLP toxicology studies are conducted using different animal species.

Example 30

In Vitro Anti-Bacterial Activity

A standard microdilution method (NCCLS, 2000; Document M7-A5) was used to determine the minimum inhibitory concentrations (MICs) against *S. aureus*, methicillin-resistant strains (MRSA); 1A-218, 1A-318, 1B-374, 1B-315, 1B-185, 1B387 (Simor et al. 1999 *Can Commun Dis Rep;* 25:105-108) and methicillin-sensitive strains (MSSA); ATCC-6538 and ATCC-29213. The MICs of some compounds were also determined against other Gram-positive bacteria: *Enterococcus faecium* (ATCC 51559), *Enterococcus faecalis* (ATCC-51299, ATCC-29212) and *Staphylococcus epidermidis* (ATCC-35983).

Mueller-Hinton broth (MHB) is recommended as the medium of choice for susceptibility testing of commonly isolated, rapidly growing aerobic organisms such as the Gram-positive bacteria included in this study. A "cation-adjusted Mueller-Hinton broth" (Ca-MHB) was prepared by first preparing standard MHB from a dehydrated base as recommended by the manufacturer. After the broth was autoclaved at 121° C. for 20 min, it was allowed to cool down to 25° C. or lower before aseptically adding $Ca^{++}$ and $Mg^{++}$ (20 mg of $Ca^{++}$/L and 10 mg of $Mg^{++}$/L).

Single colonies from fresh agar plates of the different bacterial cultures were sub-cultured overnight in 3 ml of Tryptic soy broth (TSB) at 37° C. with shaking at 250 RPM. After 18-20 hours of incubation, the absorbance at $\lambda$=600 nm ($OD_{600}$) were determined for each culture and adjusted to a final $OD_{600}$=0.1 ($4.2 \times 10^7$ cfu/ml). Bacterial suspensions were then diluted 1:200 in sterile Ca-MHB for the in vitro susceptibility test, with each well of the microtitre plate containing approximately $2 \times 10^5$ cfu/ml.

Stock solutions of the different test compounds were prepared at concentrations of 1,280 μg/ml, 640 μg/ml, or 320 μg/ml in 50% DMSO (dimethyl sulfoxide). Serial two-fold dilutions were then prepared in 50% DMSO (the working concentrations were 1:10 of the stock concentrations in 100 μl culture suspensions). The filled microtitre plates were sealed in plastic bags and incubated at 35° C. for 24 hr in an ambient air incubator with shaking at 250 RPM. MIC values were determined as the lowest concentration where complete inhibition of the visible bacterial growth was observed by the unaided eye and confirmed by the measurement of the optical density ($OD_{600}$). Table 3 shows the MIC values in μg/ml of different compounds, the MIC value provided is against all 8 strains of *S. aureus* tested except where indicated otherwise. Table 4 shows the MIC values of 3 compounds selected as examples against other gram-positive bacteria, including 2 strains resistant to the first line antibiotic vancomycin.

TABLE 3

| Compound | MIC(μg/ml) |
| --- | --- |
| 2 | 8-16 |
| 5 | >128 |
| 7 | 4-16 |
| 9 | 8 |
| 11 | 8 |
| 13 | 2-4 |
| 15 | >128 |
| 17 | 16[1] |
| 19 | 4 |
| 21 | 8-16 |
| 23 | 4-8 |
| 25 | 32-64 |
| 27 | 32-64 |
| 29 | >128 |
| 31 | 4 |
| 33 | 4-8 |
| 35 | 8 |
| 38 | >128 |
| 40 | >128 |
| 42 | 4 |
| 44 | 8 |
| 6 | 4 |
| 8 | 2 |
| 10 | 4 |
| 20 | 2-4 |
| 26 | 2 |
| 28 | 2[2] |
| 32 | 8 |
| 34 | >128 |
| 36 | 2 |
| 39 | >128 |
| 41 | >128 |
| 43 | 4 |
| 45 | 0.5 |
| 48 | 4-8 |
| 50 | >64 |
| 51 | 16 |
| 52 | >64 |
| 53 | 1 |
| 54 | 2-4 |
| 55 | 2 |
| 56 | 1 |
| 37 | >128 |
| 46 | 4 |
| 49 | 4 |
| 83 | >128 |
| 57 | 16 |
| 58 | 4 |
| 59 | 32 |
| 60 | 64 |
| 61 | 8 |
| 62 | 2 |
| 63 | 2 |
| 64 | 4 |
| 65 | 16 |
| 66 | 2 |
| 67 | 16 |
| 68 | 32 |
| 69 | 16 |
| 70 | 8 |
| 71 | 8 |
| 72 | 0.5-2 |
| 73 | >128 |
| 74 | >128 |
| 75 | 32 |
| 47 | >128 |
| 76 | >128 |
| 77 | >128 |
| 84 | 2 |

[1] MIC was >128 against strain IA-318
[2] MIC was 4 against strain IB-315

TABLE 4

| | Compound | | | |
| --- | --- | --- | --- | --- |
| Strain | 2 | 13 | 19 | Vancomycin |
| *Enterococcus faecium* (ATCC-51559) | 16 | 32 | 8 | >128 |
| *Enterococcus faecalis* (ATCC-51299) | 16 | 32 | 8 | 32 |
| *Enterococcus faecalis* (ATCC-29212) | 16 | n.d. | 8 | 4 |
| *Staphylococcus epidermidis* (ATCC-35983) | 16 | n.d. | 4 | 2 | n.d. Not determined

Example 31

In Vivo Anti-Bacterial Activity

For in vivo studies, groups of 5-10 female ICR mice (6-7 weeks) were inoculated intraperitoneally with $3-8 \times 10^7$ CFU MRSA 1B-387 per mouse in 400 μl of 5% mucin. The test compounds at concentrations of 50 or 100 mg/kg were administered orally immediately after the bacterial inoculation and again 3 hours later. The selected dosages were administered twice daily throughout the experiment. The efficacy of the treatment was evaluated by comparison of mortality between the experimental and control groups (Table 5).

TABLE 5

| Compound | Challenge MRSA (cfu/ml/route) | Treatment schedule | Survival # mice | % |
|---|---|---|---|---|
| 10 | $3.0 \times 10^7$/I.P. | 100 mg/Kg/d | 5/5 | 100 |
| 32 | $3.0 \times 10^7$/I.P. | 100 mg/Kg/d | 2/5 | 40 |
| 34 | $3.0 \times 10^7$/I.P. | 100 mg/Kg/d | 5/5 | 100 |
| 36 | $3.0 \times 10^7$/I.P. | 100 mg/Kg/d | 4/5 | 80 |
| 43 | $3.0 \times 10^7$/I.P. | 100 mg/Kg/d | 4/5 | 80 |
| Control | $3.0 \times 10^7$/I.P. | — | 2/5 | 40 |
| 5 | $6.8 \times 10^7$/I.P. | 100 mg/Kg/d | 1/5 | 20 |
| 11 | $6.8 \times 10^7$/I.P. | 100 mg/Kg/d | 0/5 | 0 |
| 13 | $6.8 \times 10^7$/I.P. | 100 mg/Kg/d | 1/5 | 20 |
| 44 | $6.8 \times 10^7$/I.P. | 100 mg/Kg/d | 3/5 | 60 |
| 8 | $6.8 \times 10^7$/I.P. | 100 mg/Kg/d | 1/5 | 20 |
| 46 | $6.8 \times 10^7$/I.P. | 100 mg/Kg/d | 2/5 | 40 |
| 83 | $6.8 \times 10^7$/I.P. | 100 mg/Kg/d | 1/5 | 20 |
| Control | $6.8 \times 10^7$/I.P. | — | 0/5 | 0 |
| 45 | $8.0 \times 10^7$/I.P. | 200 mg/Kg/d | 4/10 | 40 |
| 45 | $8.0 \times 10^7$/I.P. | 100 mg/Kg/d | 1/10 | 20 |
| Control | $8.0 \times 10^7$/I.P. | — | 0/10 | 0 |
| 29 | $7.6 \times 10^7$/I.P. | 100 mg/Kg/d | 1/5 | 20 |
| 33 | $7.6 \times 10^7$/I.P. | 100 mg/Kg/d | 0/5 | 0 |
| 35 | $7.6 \times 10^7$/I.P. | 100 mg/Kg/d | 2/50 | 40 |
| 42 | $7.6 \times 10^7$/I.P. | 100 mg/Kg/d | 0/5 | 0 |
| 6 | $7.6 \times 10^7$/I.P. | 100 mg/Kg/d | 2/5 | 40 |
| Control | $7.6 \times 10^7$/I.P. | — | 0/5 | 0 |

Example 32

In Vitro Anti-fungal Activity

A microdilution method was used to determine the anti-fungal activity of different test compounds against *Candida albicans* (ATCC 24433) at 25 µg/ml. RPMI-1640 broth is recommended as the medium of choice for susceptibility testing of *C. albicans* (NCCLS, 2002; Document M27-A2) and was used in this study. The broth was buffered to pH 7.0 and then sterilized using a 250 ml vacuum driven disposable 0.45 um filtration system.

*C. albicans* was sub-cultured from a −80° C. stock onto Sabouraud dextrose agar and incubated for 24-48 hrs at 37° C. The fungi inoculum was prepared by picking five colonies of ~1 mm in diameter from 24-48 hr old cultures. The colonies were then suspended in 5 ml of sterile normal saline (8.5 g/L NaCl; 0.85% saline) diluted 1:50 and further diluted 1:20 with medium to obtain two-fold inoculum ($1\text{-}5 \times 10^3$ cfu/ml). For MIC determinations, aliquots of this suspension placed in microtitre wells were diluted 1:1 with serial dilutions of the test compounds (the final inoculum size was $0.5\text{-}2.5 \times 10^3$ cfu/ml). The microtitre plates were then sealed in plastic bags and incubated at 35° C. for 24-48 hrs in an ambient air incubator with shaking at 250 RPM.

Inhibition of visible growth of *C. albicans* in the microtitre plate wells was assessed by the unaided eye and confirmed by $OD_{600}$ reading. Table 6 shows the anti-fungal activity of some derivatives against *C. albicans* (ATCC 24433) at a single concentration of 25 µg/ml. The MIC values of compounds with significant activity are also included.

TABLE 6

| Compound (25 µg/ml) | Inhibition (%) after 24 h | Inhibition (%) after 48 h | MIC (µg/ml) |
|---|---|---|---|
| 5 | 0 | 0 | |
| 11 | 27 | 28 | |
| 13 | 0 | 0 | |
| 29 | 0 | 0 | |
| 33 | 0 | 0 | |
| 35 | 100 | 73 | |
| 42 | 77 | 43 | |
| 44 | 0 | 0 | |
| 6 | 0 | 0 | |
| 8 | 100 | 100 | 8 |
| 10 | 0 | 0 | |
| 32 | 93 | 100 | 8 |
| 34 | 0 | 0 | |
| 36 | 86 | 97 | 16 |
| 43 | 87 | 59 | 8 |
| 46 | 33 | 0 | |
| 83 | 0 | 0 | |

The embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A compound of the structural formula:

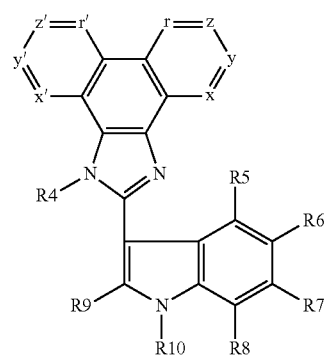

VI or a salt thereof, wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano;

R10 is H, alkyl, substituted alkyl, alkenyl, substituted alkenyl, alkynyl, substituted alkynyl, aryl, substituted aryl, heteroaryl, substituted heteroaryl, or acyl;

x is CR11;
y is CR12 or N;
z is CR13 or N;
r is CR14 or N;
x' is CR15;
y' is CR16 or N;
z' is CR17 or N;
r' is CR18 or N; and
R11, R12, R13, R14, R15, R16, R17 and R18 are independently selected from hydrogen, halogen, hydroxyl, thiol, lower alkyl, substituted lower alkyl, lower alkenyl, lower alkynyl, alkylalkenyl, alkyl alkynyl, alkoxy, alkylthio, acyl, aryloxy, amino, amido, carboxyl, aryl, substituted aryl, heterocycle, heteroaryl,
substituted heterocycle, heteroalkyl, cycloalkyl, substituted cycloalkyl, alkylcycloalkyl, alkylcycloheteroalkyl, nitro, or cyano;
wherein at least one of y, z, r, y', z' or r' is N.

2. The compound according to claim 1, wherein:
x is CR11;
y is CR12;
z is CR13;
r is N;
x' is CR15;
y' is CR16;
z' is CR17; and
r' is N.

3. The compound according to claim 1, wherein:
R11, R12, R13, R15, R16 and R17 are independently hydrogen or halogen.

4. The compound according to claim 1, wherein:
R11, R12, R13, R15, R16 and R17 are each hydrogen.

5. The compound according to claim 1, wherein:
R5, R6, R7, R8, and R9 are independently hydrogen, halogen, lower alkyl, amino, carboxyl, or nitro.

6. The compound according to claim 1, wherein:
R5, R6, R7, R8, and R9 are independently hydrogen, halogen, lower alkyl or carboxyl.

7. The compound according to claim 1, wherein:
R5, R6, R7, R8, and R9 are independently hydrogen, halogen or lower alkyl.

8. The compound according to claim 1, wherein:
R6 is hydrogen or halogen;
R9 is hydrogen or lower alkyl; and
R5, R7, R8 and R10 are each hydrogen.

9. The compound according to claim 1, wherein:
R4 is hydrogen or acyl.

10. The compound according to claim 1, wherein:
R4 is hydrogen.

11. The compound according to claim 1, wherein:
x is CR11;
y is CR12;
z is CR13;
r is N;
x' is CR15;
y' is CR16;
z' is CR17;
r' is N;
R11, R12, R13, R15, R16, and R17 are each hydrogen;
R5, R6, R7, R8, and R9 are independently hydrogen, halogen or lower alkyl, and
R4 is hydrogen or acyl.

12. The compound according to claim 11, wherein:
R4 is hydrogen.

13. The compound according to claim 1, wherein:
x is CR11;
y is CR12;
z is CR13;
r is N;
x' is CR15;
y' is CR16;
z' is CR17;
r' is N;
R11, R12, R13, R15, R16, and R17 are each hydrogen;
R6 is hydrogen or halogen;
R9 is hydrogen or lower alkyl;
R5, R7, R8 and R10 are each hydrogen, and
R4 is hydrogen or acyl.

14. The compound according to claim 13, wherein:
R4 is hydrogen.

15. A pharmaceutical composition comprising a compound according to claim 1 and a pharmaceutically acceptable carrier or diluent.

* * * * *